US012758369B2

(12) United States Patent
Jang

(10) Patent No.: US 12,758,369 B2
(45) Date of Patent: Oct. 13, 2026

(54) MIXED REALITY DENTAL IMAGING AND GUIDANCE SYSTEM

(71) Applicant: Andrew Timothy Jang, San Mateo, CA (US)

(72) Inventor: Andrew Timothy Jang, San Mateo, CA (US)

(73) Assignee: Andrew Jang, San Mateo, CA (US)

( * ) Notice: Subject to any disclaimer, the term of this patent is extended or adjusted under 35 U.S.C. 154(b) by 209 days.

(21) Appl. No.: 18/685,423

(22) PCT Filed: Aug. 24, 2022

(86) PCT No.: PCT/US2022/075416
§ 371 (c)(1),
(2) Date: Feb. 21, 2024

(87) PCT Pub. No.: WO2023/028529
PCT Pub. Date: Mar. 2, 2023

(65) Prior Publication Data

US 2024/0350237 A1 Oct. 24, 2024

Related U.S. Application Data

(60) Provisional application No. 63/237,911, filed on Aug. 27, 2021.

(51) Int. Cl.
*A61C 9/00* (2006.01)
*A61B 34/20* (2016.01)
*G06T 19/00* (2011.01)

(52) U.S. Cl.
CPC .......... *A61C 9/0053* (2013.01); *G06T 19/006* (2013.01); *A61B 2034/2055* (2016.02)

(58) Field of Classification Search
CPC ................ A61C 9/0053; G06T 19/006; A61B 2034/2055
See application file for complete search history.

(56) References Cited

U.S. PATENT DOCUMENTS

| | | | | |
|---|---|---|---|---|
| 9,622,699 | B2 * | 4/2017 | Hultgren | G16H 40/67 |
| 11,045,138 | B2 * | 6/2021 | Hultgren | A61C 19/05 |
| 12,369,847 | B2 * | 7/2025 | Hultgren | A61B 5/228 |

(Continued)

FOREIGN PATENT DOCUMENTS

| | | |
|---|---|---|
| WO | WO-2020160461 A1 | 8/2020 |
| WO | WO-2023028529 A1 | 3/2023 |

OTHER PUBLICATIONS

"International Application Serial No. PCT/US2022/075416, International Search Report mailed Jan. 24, 2023", 4 pgs.

(Continued)

*Primary Examiner* — Utpal D Shah
(74) *Attorney, Agent, or Firm* — SCHWEGMAN LUNDBERG & WOESSNER, P.A.

(57) ABSTRACT

An imaging system is described. In one aspect, a method includes accessing pressure sensor data from a pressure sensor being bitten by a patient, accessing occlusal pattern data corresponding to the patient, correlating the pressure sensor data with the occlusal pattern data, and identifying a location of the pressure sensor relative to the teeth of the patient based on the correlated pressure sensor data with the occlusal pattern data.

19 Claims, 39 Drawing Sheets

(56) References Cited

U.S. PATENT DOCUMENTS

| | | | | |
|---|---|---|---|---|
| 2012/0015316 | A1 * | 1/2012 | Sachdeva | A61B 1/24 382/128 |
| 2013/0052609 | A1 * | 2/2013 | Kume | A61C 19/05 433/71 |
| 2017/0290699 | A1 * | 10/2017 | Radmand | A61B 5/4557 |
| 2020/0250819 | A1 * | 8/2020 | Jang | G06T 7/0012 |
| 2025/0114035 | A1 * | 4/2025 | Hu | A61B 5/4818 |

OTHER PUBLICATIONS

"International Application Serial No. PCT/US2022/075416, Invitation to Pay Additional Fees mailed Nov. 10, 2022", 2 pgs.

"International Application Serial No. PCT/US2022/075416, Written Opinion mailed Jan. 24, 2023", 8 pgs.

"International Application Serial No. PCT/US2022/075416, International Preliminary Report on Patentability mailed Mar. 7, 2024", 10 pgs.

* cited by examiner

MIXED REALITY DENTAL IMAGING AND GUIDANCE SYSTEM

CROSS-REFERENCE TO RELATED APPLICATION

The present application is a U.S. National Stage Filing under 35 U.S.C. 371 from International Application No. PCT/US2022/075416, filed on 24 Aug. 2022, and published as WO 2023/028529 on 2 Mar. 2023, which application claims priority to U.S. Provisional Patent Application Ser. No. 63/237,911, filed Aug. 27, 2021, each of which are incorporated herein by reference in their entireties.

BACKGROUND

The subject matter disclosed herein generally relates to the processing of data. Specifically, the present disclosure addresses systems and methods for generating mixed reality imaging and providing guidance visualization.

Current techniques for assessing periodontal health involves a dentist manually measuring gum disease of a patient at different points with a dental instrument. This manual procedure does not allow the dentist or the patient to easily visualize a current state of gum disease of the patient.

Furthermore, current techniques for taking x-ray pictures of teeth of a patient involve a technician estimating an area of interest, and placing an x-ray sensitive film or sensor at the estimated location in the mouth of the patient. However, inaccurate placement of the x-ray sensitive film or sensor, or the x-ray source can result in the technician having to re-adjust the location of the x-ray sensitive film, the sensor, the x-ray source and taking additional x-ray pictures. Such additional x-ray pictures lead to unnecessary exposure to radiation and can potentially harm the health of the patient.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
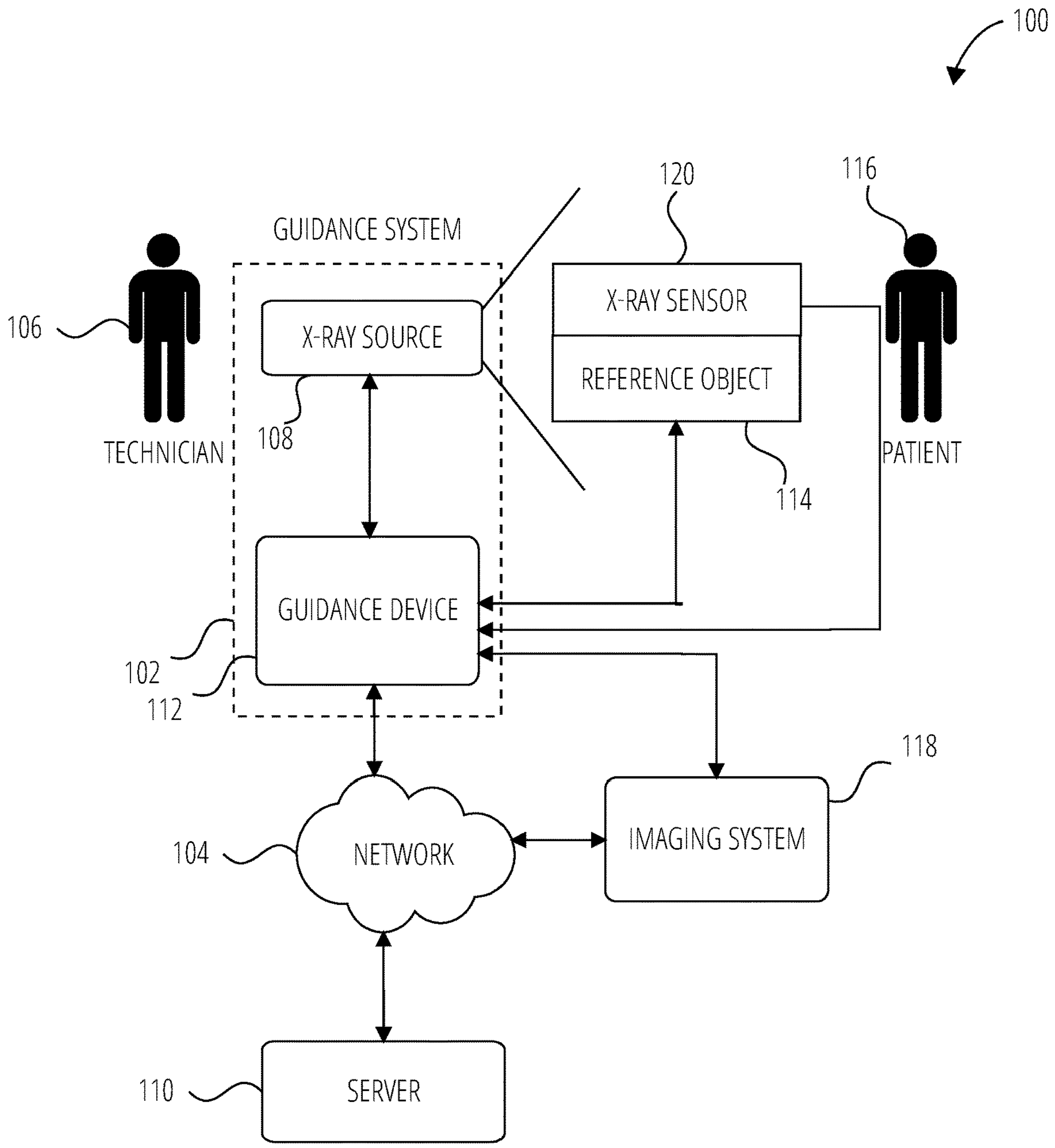
FIG. 1 illustrates a network environment for operating an imaging system and a guidance system in accordance with one example embodiment.

Example methods and systems are directed to a method for generating dental imaging with augmented information and generating guidance visualization. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

The present application describes a method for generating dental imaging with augmented information and generating guidance visualization. In one example, the present application describes an imaging system that provides diagnostic information regarding a patient's oral periodontal health. Current methods are slow, painful, and inaccurate (e.g., a dentist pokes a patient's gum line with a little thin stick and calls out arbitrary numbers). The information from different imaging techniques (e.g., intraoral scanner and cone beam computerized tomography) is combined and provides additional information that cannot be determined using the individual components separately. In a further example, the imaging system accesses updated images (e.g., x-ray) and updates the composite image based on the updated images. As such, the imaging system provides a comprehensive assessment of a person's periodontal health and individualized anatomical landmarks based on multiple imaging sources and augment a clinician's clinical tools (e.g., handpiece) to virtually interact/position itself in the same digital workspace.

In another example, the present application describes a guidance system that provides directions/cues/visual guidance feedback information to a technician to adjust a placement/location of an x-ray sensor, a bite block, a x-ray source based on simulated images using the relative location of the x-ray source, the x-ray sensor, and a bite block positioned in the mouth of a patient. In a further example, the guidance system displays a virtual positioning of a dental instrument in relation to a particular "region of interest" for a dental procedure. For example, a region of interest may include a location of cavities when drilling a filling (also can be used to locate tooth nerve when performing a filling), a location of bone for implant placement, and a location of target nerve for tough anesthetic injections. Currently, the dentist assesses or estimates the region of interest based on visible external landmarks in the mouth of the patient.

Example advantages of digital diagnosis include:

- imaging can be performed by auxiliary dental staff, accurate than the traditional methods of measuring gum diseases (3 point measurements on the gum) which makes it easy to miss;
- easier visualization by the doctor and patients (patient education and easier to "sell" treatment);
- quantity different markers of periodontal (e.g., gum) health instantaneously. The imaging data can be used to improve gum measurement over time (e.g., via machine learning model) and visualize health trends.

Example advantage of mixed reality for dental tools include:

- more precise than just guessing using local landmarks;
- can be used to definitively avoid problem areas (e.g., nerve chamber when drilling a tooth for a filling);
- can be used for multiple types of dental procedures (e.g., fillings, crown preps, injections)—system can be used with interchangeable parts;
- can be integrated into normal dental workflow (uses tools that dentists are comfortable with).

In one example embodiment, the present application describes a method comprising: accessing pressure sensor data from a pressure sensor being bitten by a patient; accessing occlusal pattern data corresponding to the patient; correlating the pressure sensor data with the occlusal pattern data; and identifying a location of the pressure sensor relative to the teeth of the patient based on the correlated pressure sensor data with the occlusal pattern data.

In another example embodiment, a non-transitory machine-readable storage device may store a set of instructions that, when executed by at least one processor, causes the at least one processor to perform the method operations discussed within the present disclosure.

FIG. 1 is a network diagram illustrating a network environment 100 suitable for operating a guidance system 102 and an imaging system 118, according to some example embodiments. The network environment 100 includes the guidance system 102, the imaging system 118 and a server 110, communicatively coupled to each other via a network 104. The guidance system 102, the imaging system 118, and the server 110 may each be implemented in a computer system, in whole or in part, as described below with respect to FIG. 39.

The server 110 may be part of a network-based system. For example, the network-based system may be or include a cloud-based server system that provides additional information, such as three-dimensional models of specimens, updated imaging data from other sources, and any additional data related to a patient 116 to the guidance system 102 and the imaging system 118.

FIG. 1 illustrates a technician 106 using the guidance system 102 and the imaging system 118. The technician 106 may be a human user (e.g., a human being), a machine user (e.g., a computer configured by a software program to interact with an x-ray source 108), or any suitable combination thereof (e.g., a human assisted by a machine or a machine supervised by a human). The technician 106 is not part of the network environment 100, but is associated with the guidance system 102 and may be a technician 106 of the guidance system 102.

The guidance system 102 includes an x-ray source 108 and a guidance device 112. The x-ray source 108 includes a source of radiation that generates x-ray that are directed to the mouth of the patient 116. The guidance device 112 may be a computing device with a display such as a tablet computer, a laptop computer, a desktop computer. The guidance device 112 generates a simulated output of an x-ray image based on the location of the x-ray source 108 relative to the location of the x-ray sensor 120 based on the location of a reference object 114. The x-ray sensor 120 is coupled to the reference object 114 at a predetermined location. The location of the reference object 114 relative to the teeth of the patient 116 is predetermined (e.g., based on a mold of the teeth of the patient). The guidance device 112 provides feedback to the technician 106 as to whether the placement of the x-ray source 108 relative to the x-ray sensor 120 will generate an acceptable x-ray image.

In another example embodiment, the guidance system 102 includes a dental instrument (not shown) such as a dental hand piece, scalpel, syringe. The guidance device 112 determines the location of the dental instrument relative to the mouth of the patient 116 and generates a mixed reality visualization of the dental instrument relative to synthetic data overlaid on a real-time, near real-time image of the teeth/mouth of the patient.

In another example embodiment, the guidance system 102 generates a visualization of a gum disease to the technician 106. In one example embodiment, the region of interest includes a mouth/gum/teeth of a patient 116. The reference object 114 is temporarily coupled to the mouth of the patient 116. For example, the reference object 114 includes a custom-bite block that the patient 116 bites.

In another example embodiment, the x-ray source 108 is capable of tracking its relative position and orientation in space relative to the reference object 114. For example, the x-ray source 108 includes optical sensors (e.g., depth-enabled 3D camera, image camera), inertial sensors (e.g., gyroscope, accelerometer), wireless sensors (Bluetooth, Wi-Fi), and GPS sensor, to determine the location of the x-ray source 108 within a real world environment. In another example, the location, position, and orientation of the x-ray source 108 is determined relative to the reference object 114 (e.g., an object that is coupled and remains temporarily fixed to the teeth of a patient).

The imaging system 118 includes a computing device that generates a composite image based on different imaging sources. For example, a first source includes volumetric data and a second source includes surface data. The imaging system 118 generates a composite image based on the first and second sources. The composite image indicates the volumetric data and the surface data of the specimen. In one example, the first source includes a cone beam CT scanner that indicates bone volume of the specimen. The second source includes an intraoral scanner.

In one example embodiment, the imaging system 118 accesses third imaging data of a prepped tooth. The third imaging data includes a digital surface scan of the prepped tooth. The imaging system 118 identifies features from teeth adjacent to the prepped tooth. The imaging system 118 registers the third imaging data with the composite image based on the features of the teeth adjacent to the prepped tooth. The imaging system 118 identifies an intersection of external treatment tooth geometry and the registered third imaging data. The imaging system 118 determines a crown margin based on the identified intersection.

Any of the machines, databases, or devices shown in FIG. 1 may be implemented in a general-purpose computer modified (e.g., configured or programmed) by software to be a special-purpose computer to perform one or more of the functions described herein for that machine, database, or device. For example, a computer system able to implement any one or more of the methodologies described herein is discussed below with respect to FIG. 6 to FIG. 13. As used herein, a “database” is a data storage resource and may store data structured as a text file, a table, a spreadsheet, a relational database (e.g., an object-relational database), a triple store, a hierarchical data store, or any suitable combination thereof. Moreover, any two or more of the machines, databases, or devices illustrated in FIG. 1 may be combined into a single machine, and the functions described herein for any single machine, database, or device may be subdivided among multiple machines, databases, or devices.

The network 104 may be any network that enables communication between or among machines (e.g., server 110), databases, and devices (e.g., guidance device 112, imaging system 118). Accordingly, the network 104 may be a wired network, a wireless network (e.g., a mobile or cellular network), or any suitable combination thereof. The network 104 may include one or more portions that constitute a private network, a public network (e.g., the Internet), or any suitable combination thereof.

Figure 2:
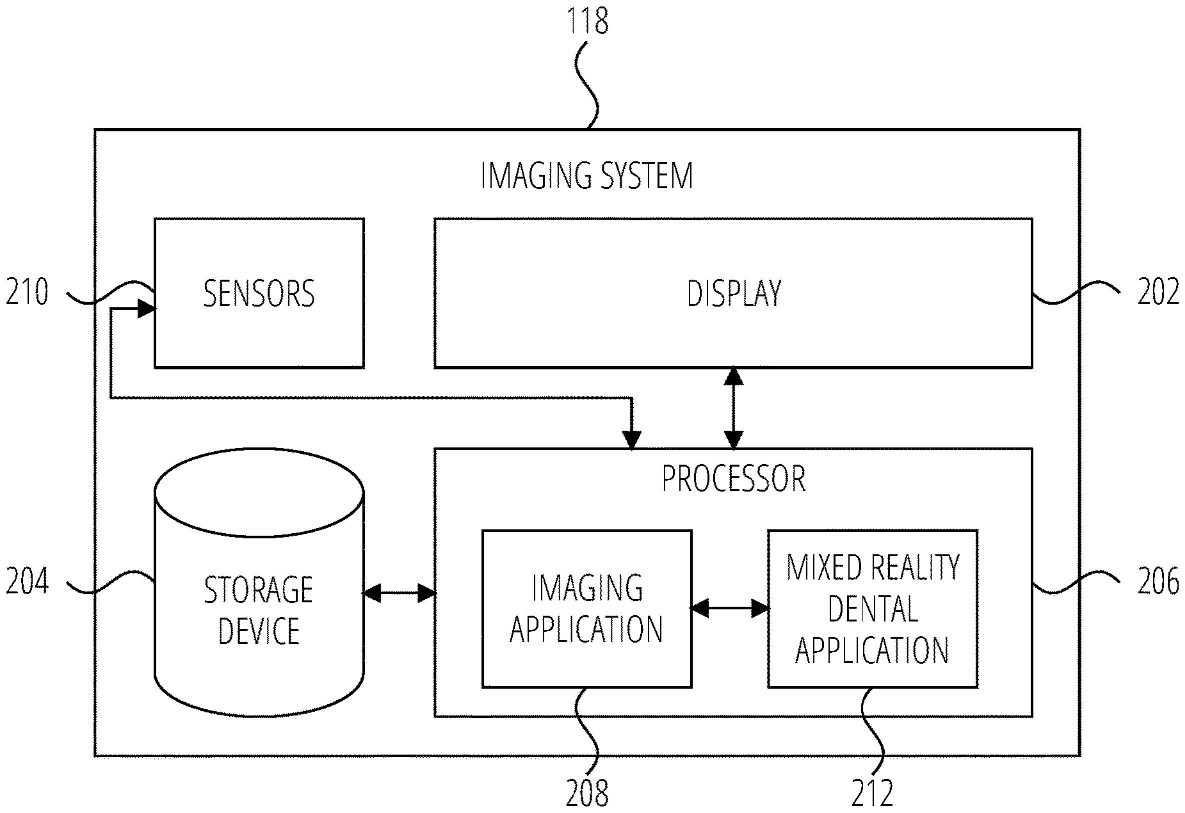
FIG. 2 illustrates an imaging system in accordance with one example embodiment.

FIG. 2 is a block diagram illustrating modules (e.g., components) of the guidance system 102, according to some example embodiments. The guidance system 102 includes sensors 210, a display 202, processor 206, and a storage device 204. The sensors 210 includes, for example, optical sensors and inertial sensors. The display 202 displays a composite image or simulated x-ray image.

The processor 206 includes an imaging application 208 and a mixed reality dental application 212. The imaging application 208 generates a composite image based on different imaging sources (e.g., intraoral and CBCT). For example, a first source includes volumetric data and a second source includes surface data. The imaging application 208 generates a composite image based on the first and second sources. The composite image indicates the volumetric data and the surface data of the specimen. In one example, the first source includes a cone beam CT scanner that indicates bone volume of the specimen. The second source includes an intra oral scanner.

In one example embodiment, the imaging application 208 accesses third imaging data of a prepped tooth. The third imaging data includes a digital surface scan of the prepped tooth. The imaging application 208 identifies features from teeth adjacent to the prepped tooth. The imaging application 208 registers the third imaging data with the composite image based on the features of the teeth adjacent to the prepped tooth. The imaging application 208 identifies an intersection of external treatment tooth geometry and the registered third imaging data. The imaging application 208 determines a crown margin based on the identified intersection.

The mixed reality dental application 212 generates augmented information based on the location of a dental instrument and the three-dimensional model of the teeth and gum of the patient 116. For example, the processor 206 displays a virtual representation of the dental instrument relative to the 3D model of the mouth of the patient 116 (e.g., teeth and gum of the patient 116). In one example, the location of the x-ray source 108 is determined relative to the reference object 114 based on the sensors in dental instrument and reference object 114.

In other example embodiment, the mixed reality dental application 212 can be used for medical and surgical procedures to display in real-time an image of a surgical instrument operated by a medical professional in relation to digital information that indicate an area of interest on a real-time image of a body part of the patient.

In other example embodiment, the mixed reality dental application 212 indicates a region of interest in a display of the 3D model. For example, the mixed reality dental application 212 indicates a tooth decay area in a display of the 3D model, a suggested shape for a root canal in a display of the 3D model, regions of the tooth for removal for a crown procedure in a display of the 3D model, or a bone region of a projected injection site in a display of the 3D model.

In other example embodiment, the composite image includes a visual indication of the region of the interest (e.g., gingival surface). The mixed reality dental application 212 generates augmented information based on the location of the dental instrument and the three-dimensional model of the teeth and gum of the patient.

As such, the mixed reality dental application 212 merges information from the real and virtual world to produce new environments and visualizations, where physical and digital objects co-exist and interact in real-time. Mixed reality is a hybrid of augmented reality (AR) and virtual reality (VR). In one example, the mixed reality dental application 212 includes a combination of AR and VR aspects.

In one example embodiment, the imaging system 118 may communicate over the network 104 with the server 110 to retrieve a portion of a database of visual references (e.g., images from different specimens).

Any one or more of the modules described herein may be implemented using hardware (e.g., a processor of a machine) or a combination of hardware and software. For example, any module described herein may configure a processor to perform the operations described herein for that module. Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices.

Figure 3:
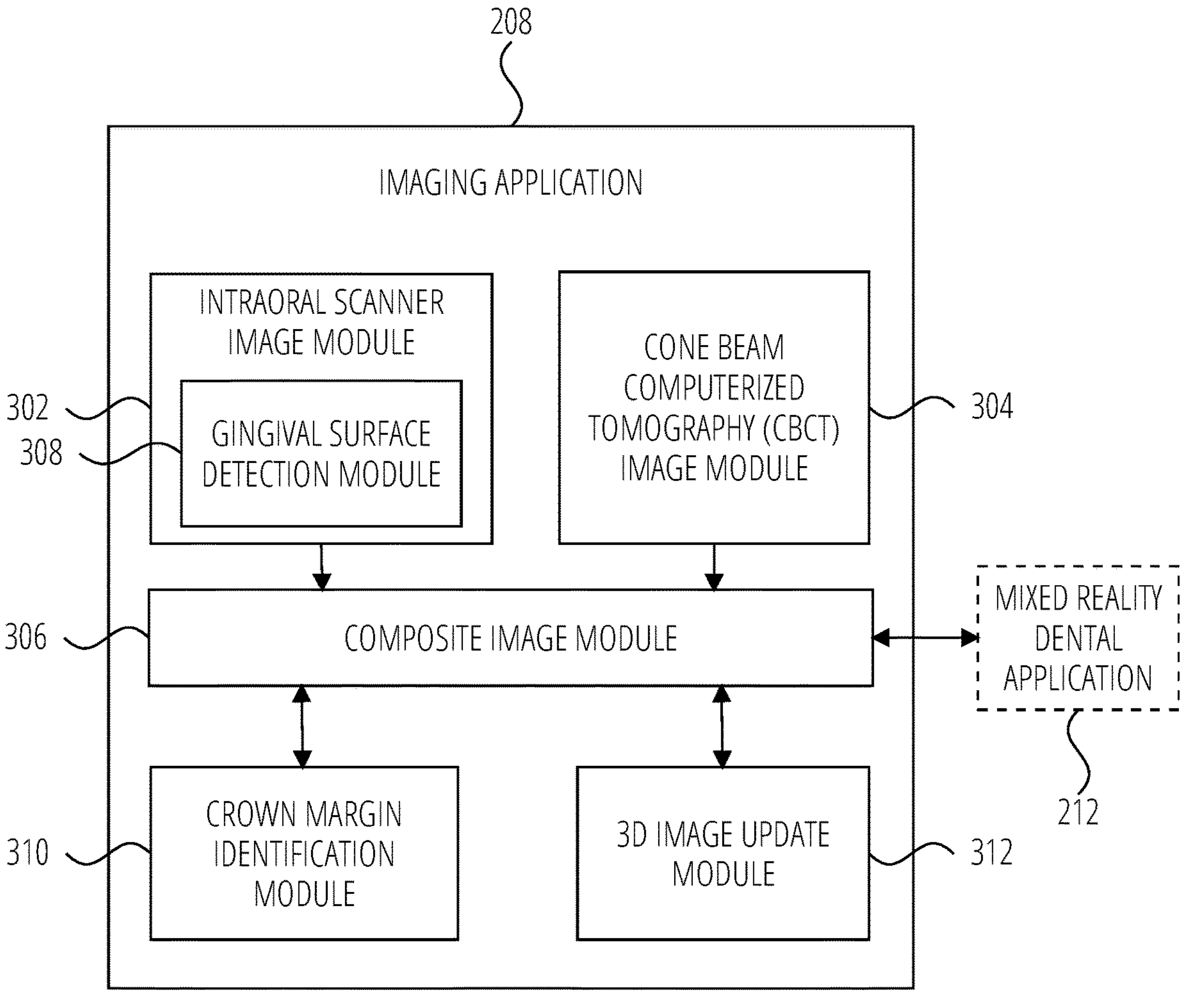
FIG. 3 illustrates an imaging application in accordance with one example embodiment.

FIG. 3 illustrates an imaging application in accordance with one example embodiment. The imaging application 208 generates a composite image based on different image sources (e.g., intraoral and CBCT). The composite image includes a visual indication of the region of the interest (e.g., gingival surface). In one example, the imaging application 208 comprises an intraoral scanner image module 302, a cone beam computerized tomography (CBCT) image module 304, a composite image module 306, a gingival surface detection module 308, a crown margin identification module 310, and a 3D image update module 312.

The intraoral scanner image module 302 communicates with an intraoral scanner and accesses first image data of the patient 116 from the intraoral scanner. Examples of intraoral scanner include, but are not limited to, light projection and capture, laser confocal, AWS (Active Wavefront Sampling), and stereo-photogrammetry.

The intraoral scanner image module 302 includes a gingival surface detection module 308 that detects gingival surface based on the first image data. For example, the gingival surface detection module 308 determines depth of tissue based on the image data and compares the depth of tissue to a predefined lookup table of gingival depth.

The cone beam computerized tomography (CBCT) image module 304 communicates with a cone beam computerized tomography (CBCT) and accesses second image data of the patient 116 from the CBCT.

The composite image module 306 generates a composite image (of the patient 116's teeth/gum) based on the first image data from the intraoral scanner image module 302 and the second image data from the cone beam computerized tomography (CBCT) image module 304. In one example, the composite image module 306 uses image segmentation, image registration/alignment of images to generate the composite image. For example, the composite image module 306 identifies a common region of the specimen in the first imaging data and the second imaging data and aligns the first imaging data with the second imaging data based on the identified common region. The composite image module 306 registering the composite image when the common region of the specimen are aligned in the imaging data. The composite image module 306 communicates the composite image to the mixed reality dental application 212.

The crown margin identification module 310 identifies and generates a visualization of acceptable crown margins based on the data from the composite image and other sources (e.g., updated teeth images).

The 3D image update module 312 accesses an x-ray image of teeth of the patient 116, matches the location of the x-ray image relative to the composite image, and updates the composite image based on the x-ray image.

Figure 4:
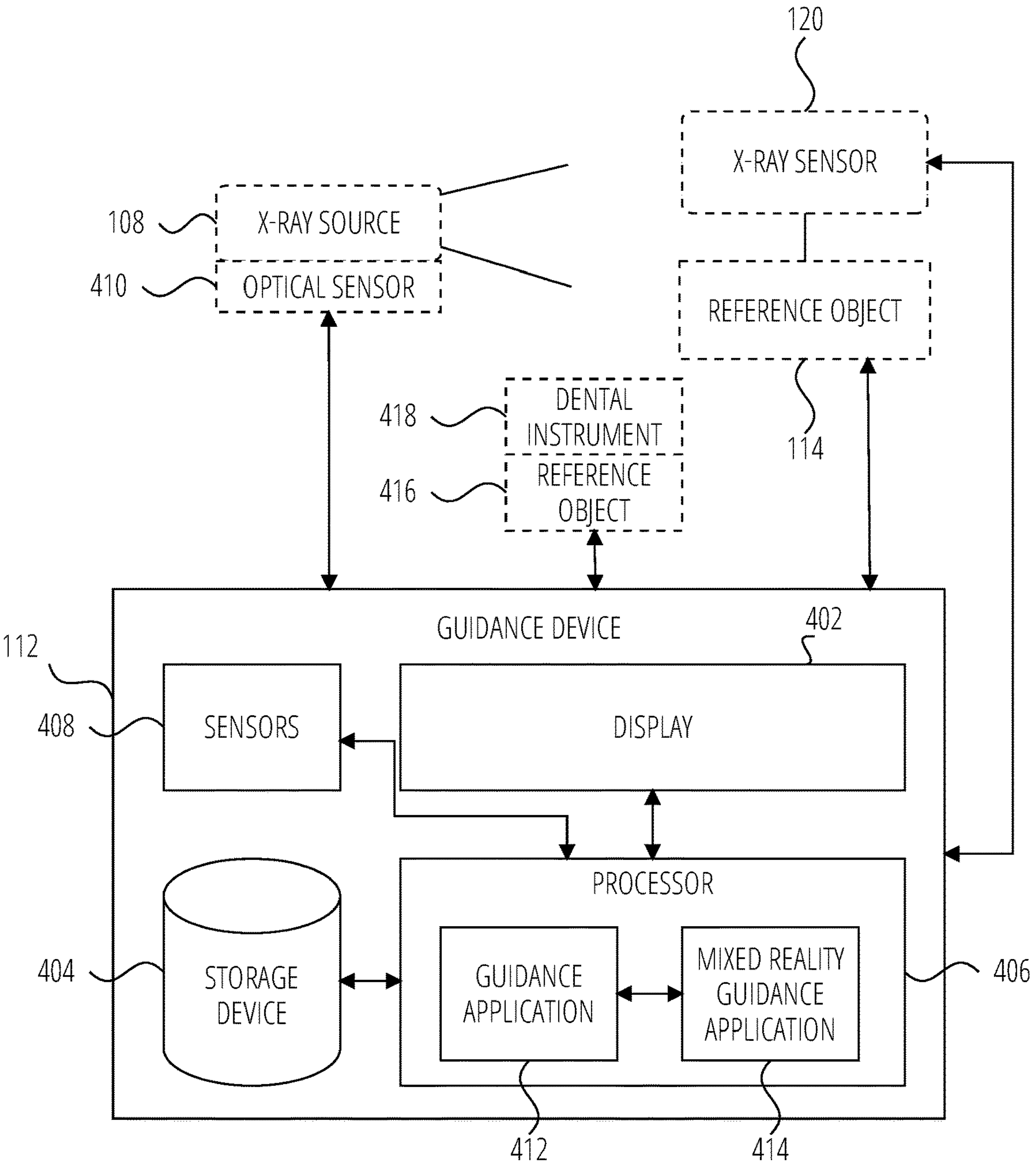
FIG. 4 illustrates a guidance device in accordance with one example embodiment.

FIG. 4 illustrates a guidance device in accordance with one example embodiment. The guidance device 112 includes sensors 408, a display 402, a storage device 404, and a processor 406. The processor 406 includes a guidance application 412 and a mixed reality guidance application 414. The guidance device 112 communicates with the x-ray source 108/optical sensor 410, x-ray sensor 120/reference object 114, and dental instrument 418/reference object 416.

The guidance application 412 displays a simulated x-ray image based on the x-ray source 108 relative to the x-ray sensor 120. In one example, the location of the x-ray source 108 is determined relative to the reference object 114 based on the sensors in x-ray source 108 and reference object 114.

The guidance application 412 provides feedback of the location of the x-ray source 108 relative to the x-ray sensor 120, or the location of the dental instrument 418 relative to the reference object 114. The feedback may be in the form of directional indicators that prompt the technician 106 to move the x-ray source 108 or the dental instrument 418 in a guided direction relative to the mouth of the patient 116 (or relative to the reference object 114—a bite block bitten by the patient 116).

The mixed reality guidance application 414 generates augmented information based on the location of the x-ray source 108 and the three-dimensional model of the teeth and gum of the patient 116.

In one example, the mixed reality guidance application 414 can be used for medical and surgical procedures to display in real-time an image of a surgical instrument operated by a medical professional in relation to digital information that indicate an area of interest on a real-time image of a body part of the patient.

In one example embodiment, the guidance device 112 may communicate over the network 104 with the server 110 to retrieve a portion of a database of visual references (e.g., images from different specimens).

Figure 5:
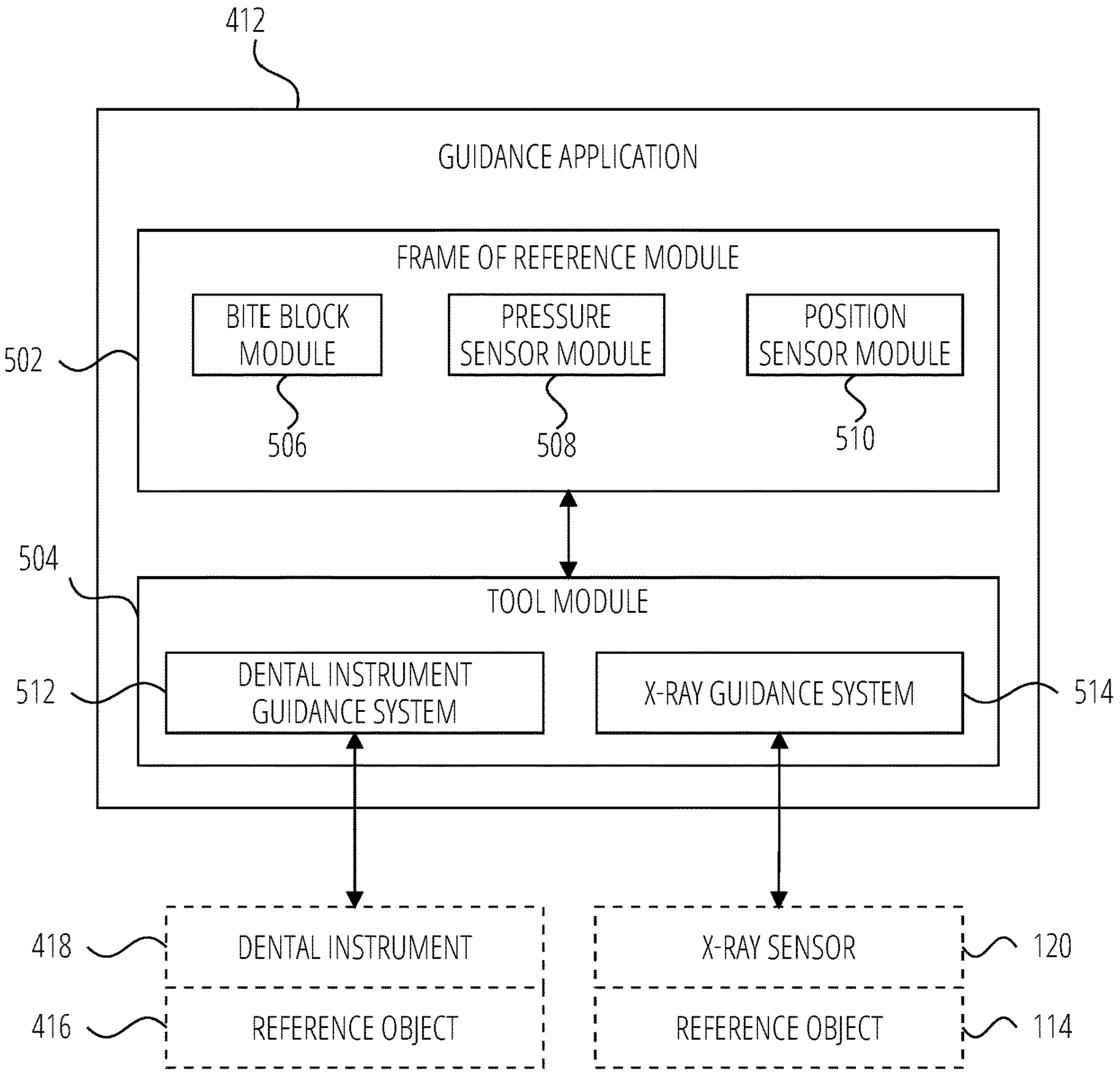
FIG. 5 illustrates a guidance application in accordance with one example embodiment.

Any one or more of the modules described herein may be implemented using hardware (e.g., a processor of a machine) or a combination of hardware and software. For example, any module described herein may configure a processor to perform the operations described herein for that module. Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices. FIG. 5 illustrates a guidance application in accordance with one example embodiment. The guidance application 412 includes a frame of reference module 502, and a tool module 504. The frame of reference module 502 determines a location of the x-ray sensor 120 relative to the location of the x-ray source 108 based on sensors in the reference object 114 (or in the x-ray source 108). In one example, the sensors include a combination of a gyroscope, an accelerometer, inertial sensor, wireless communication device (e.g., bluetooth, wifi), or any other sensor that detects a position, location, orientation of the x-ray source 108 relative to the x-ray sensor 120 and the reference object 114.

The frame of reference module 502 identifies a location of the teeth of the patient 116 relative to a reference object 114 temporarily coupled to the teeth of the patient 116 (e.g., bit by the patient). In one example, the frame of reference module 502 includes a bite block module 506, a pressure sensor module 508, and a position sensor module 510.

The bite block module 506 includes predetermined relative locations of the teeth relative to a custom bite block of the patient 116.

The pressure sensor module 508 detects pressure readings of a pressure sensor disposed on a generic bite block. The pressure reading indicates the pressure from individual points of the teeth on the pressure sensor. The pressure reading is used to generate a unique signature based on the bite of the patient 116 and can be used to determine the position of the teeth relative to the pressure sensor.

The position sensor module 510 includes a location sensor that identifies the location of a sensor relative to the x-ray source 108. For example, sensors in the x-ray source 108 communicate with the sensors in the reference object 114. In yet another example, the sensors in the x-ray source 108 and the sensors in the reference object 114 both communicate with the frame of reference module 502. In yet another example, the frame of reference module 502 uses the optical sensor in the x-ray source 108 to detect a position, location, orientation of the sensors in the x-ray source 108. For example, the position sensor module 510 detects a first unique visual marker of the dental instrument and a second unique visual marker of the reference object 114. The frame of reference module 502 can thus determine a relative distance, position, and orientation of the x-ray source 108 relative to the reference object 114.

In one example, the reference object 114 is at a predetermined location relative to the teeth of the patient. Sensors in the reference object 114 are located at a predefined distance related to the reference object 114. For example, the distance between an end of the reference object 114 and the sensors in the reference object 114 are predefined. In one example, the sensors may be coupled to any portion of the reference object 114. A lookup table that defines the relative distances may be updated based on the measured distances between the sensors and other portions of the reference object 114. In another example embodiment, the reference object 114 is custom-printed or custom-shaped based on the teeth of the patient.

The tool module 504 determines a relative position, location, orientation of the x-ray source 108 relative to the reference object 114 and provides feedback/guidance to the technician 106 based on the relative positions. In one example, the tool module 504 includes a dental instrument guidance system 512 and an x-ray guidance system 514. The dental instrument guidance system 512 determines the relative distance/position between a dental instrument 418/reference object 416 and the reference object 114. The dental instrument guidance system 512 accesses a 3D model (or a composite image) of the teeth/gum of the patient. The dental instrument guidance system 512 initializes and calibrates the location of the reference object 114 relative to the teeth of the patient based on the predefined distance/location between the reference object 114 relative to the teeth of the patient, and the predefined distance/location between the sensors of the dental instrument 418 relative to the reference object 114.

The dental instrument guidance system 512 determines a location of the dental instrument 418 relative to the reference object 114 based on the detected position, location, orientation of the reference object 416 relative to the reference object 114.

The dental instrument guidance system 512 causes a display of a virtual dental instrument (or any other type of visual indicator) relative to the 3D model (or composite image) of the teeth/gum of the patient 116 based on the position, location, orientation and distance of the sensors in the reference object 416 relative to the reference object 114. As such, the dental instrument guidance system 512 provides real-time feedback (of the location of the dental instrument 418) to the technician 106 (e.g., dentist) of the guidance system 102.

In another example, the dental instrument guidance system 512 causes display of a region of interest in the 3D model or composite image based on the mixed reality guidance application 414. For example, the dental instrument guidance system 512 displays the location of the dental instrument 418 relative to a highlighted region of interest in the 3D model or composite image. In another example, the dental instrument guidance system 512 provides virtual display indicators in display 202 to guide the technician 106 on how to perform a procedure (e.g., where to position and operate the dental instrument 418 on the patient 116).

The x-ray guidance system 514 determines the relative distance/position between the x-ray source 108 and the reference object 114. The x-ray guidance system 514 accesses a 3D model (or a composite image) of the teeth/gum of the patient. The x-ray guidance system 514 initializes and calibrates the location of the reference object 114 relative to the teeth of the patient based on the predefined distance/location between the reference object 114 relative to the teeth of the patient, and the predefined distance/location between the sensors of the x-ray source 108 relative to the reference object 114.

The x-ray guidance system 514 determines a location of the x-ray source 108 relative to the reference object 114 based on the detected position, location, orientation of the x-ray source 108 relative to the reference object 114.

The x-ray guidance system 514 causes a display of a simulated x-ray image based on the position, location, orientation and distance of the x-ray source 108 relative to the reference object 114. As such, the x-ray guidance system 514 provides real-time feedback (of a simulated x-ray image based on the location of the x-ray source 108 and the x-ray sensor 120) to the technician 106 (e.g., dentist).

In another example, the x-ray guidance system 514 provides feedback and provides directional guidance on the direction in which the x-ray sensor 120 or the x-ray source 108 is to be moved to generate an acceptable x-ray picture. For example, the x-ray guidance system 514 provides virtual display indicators in the display 202 to guide the technician 106 on how/where to adjust perform the x-ray sensor 120 and/or the x-ray source 108.

Once the x-ray guidance system 514 detects that an x-ray picture has been taken with the x-ray source 108, the x-ray guidance system 514 automatically labels the image with metadata describing the position of where the x-ray that was taken within the mouth. The metadata can further indicate the relative location between the x-ray source 108, the x-ray sensor 120, and the reference object 114.

Figure 6:
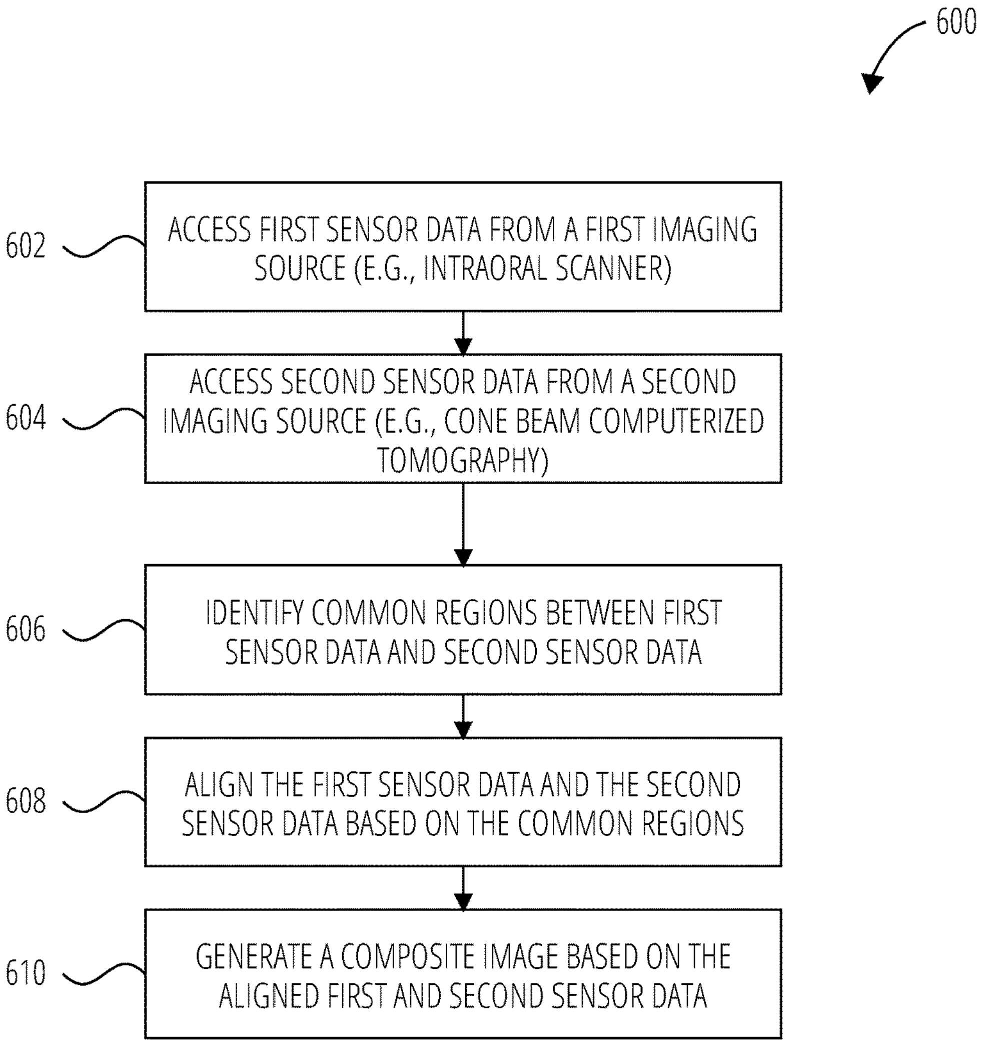
FIG. 6 illustrates a method for generating a composite image in accordance with one example embodiment.

FIG. 6 illustrates a method 600 for generating a composite image in accordance with one example embodiment. Operations in the method 600 may be performed by the composite image module 306, using components (e.g., modules, engines) described above with respect to FIG. 3. Accordingly, the method 600 is described by way of example with reference to the composite image module 306. However, it shall be appreciated that at least some of the operations of the method 600 may be deployed on various other hardware configurations or be performed by similar Components residing elsewhere.

At block 602, the composite image module 306 accesses first sensor data from a first imaging source (e.g., intraoral scanner) via intraoral scanner image module 302. At block 604, the composite image module 306 accesses second sensor data from a second imaging source (e.g., cone beam computerized tomography) via cone beam computerized tomography (CBCT) image module 304. At block 606, the composite image module 306 identifies common regions between the first sensor data and second sensor data (e.g., same parts of a tooth). At block 608, the composite image module 306 aligns the first sensor data and the second sensor data based on the common regions. At block 610, the composite image module 306 generates a composite image based on the aligned first and second sensor data.

Figure 7:
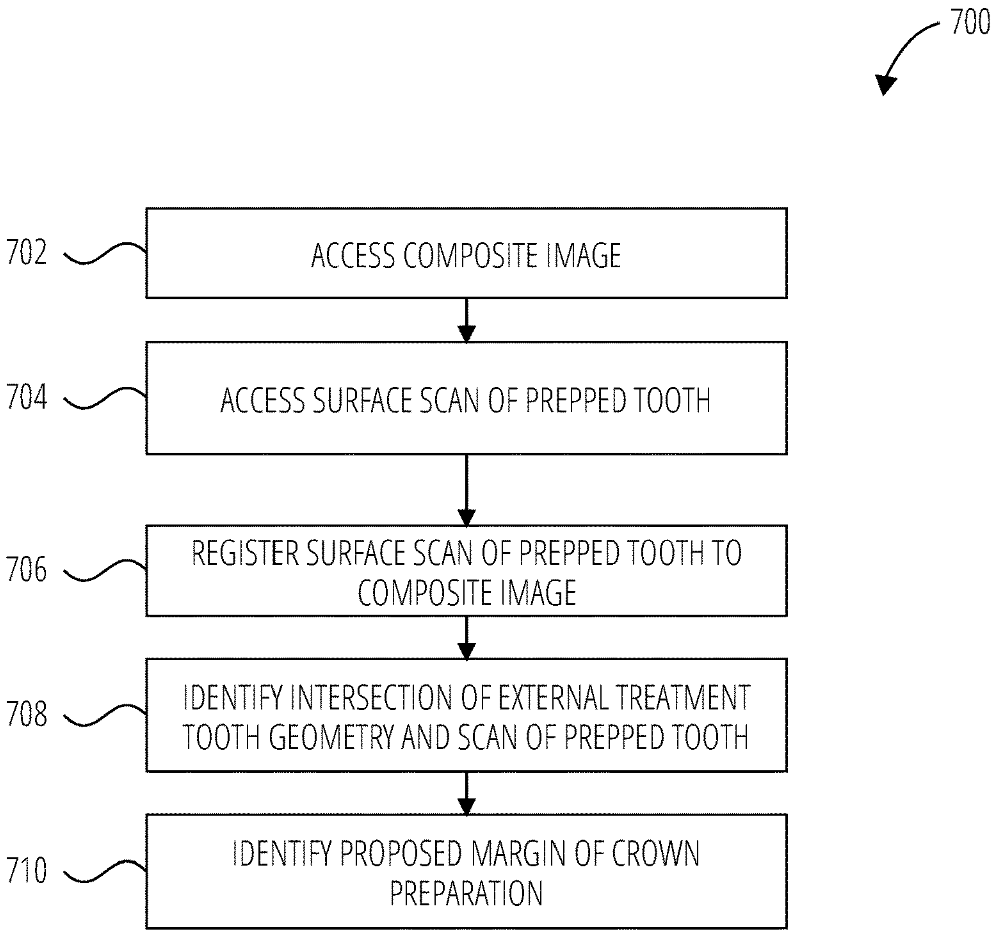
FIG. 7 illustrates a method for identifying a proposed margin of a crown in accordance with one example embodiment.

FIG. 7 illustrates a method 700 for identifying a proposed margin of a crown in accordance with one example embodiment. Operations in the method 700 may be performed by the crown margin identification module 310, using Components (e.g., modules, engines) described above with respect to FIG. 3. Accordingly, the method 700 is described by way of example with reference to the crown margin identification module 310. However, it shall be appreciated that at least some of the operations of the method 700 may be deployed on various other hardware configurations or be performed by similar Components residing elsewhere.

In block 702, the crown margin identification module 310 accesses a composite image (from composite image module 306). In block 704, the crown margin identification module 310 accesses surface scan of prepped tooth. In block 706, the crown margin identification module 310 registers the surface scan of prepped tooth to the composite image. In block 708, the crown margin identification module 310 identifies intersection of external treatment tooth geometry and scan of prepped tooth. In block 710, the crown margin identification module 310 identifies proposed margin of crown preparation.

Figure 8:
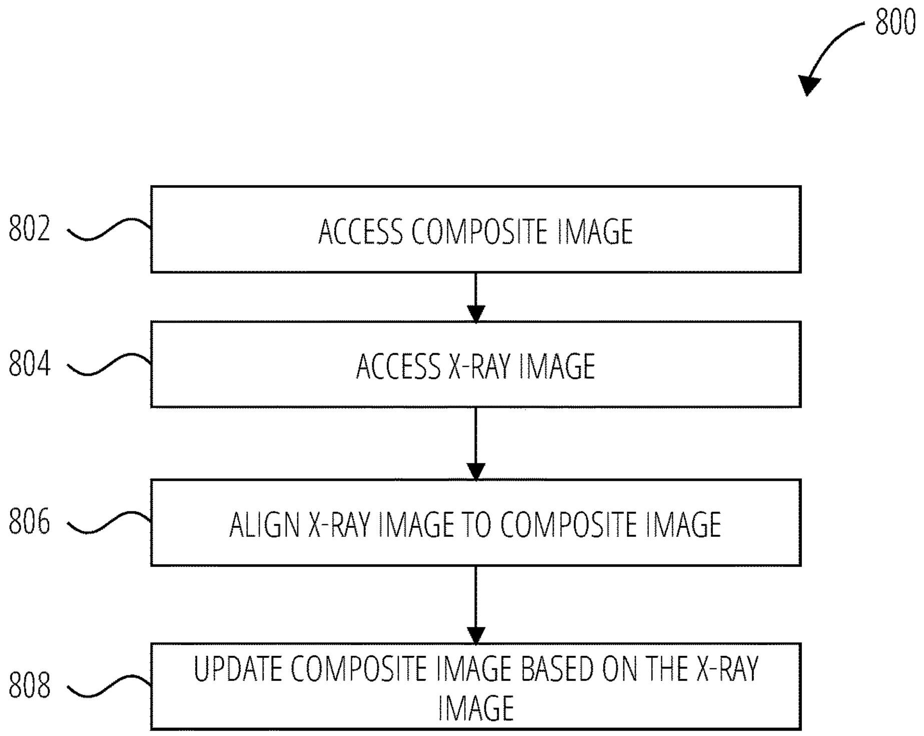
FIG. 8 illustrates a method for updating a composite image in accordance with one example embodiment.

FIG. 8 illustrates a method 800 for updating a composite image in accordance with one example embodiment. Operations in the method 800 may be performed by the 3D image update module 312, using Components (e.g., modules, engines) described above with respect to FIG. 3. Accordingly, the method 800 is described by way of example with reference to the 3D image update module 312. However, it shall be appreciated that at least some of the operations of the method 800 may be deployed on various other hardware configurations or be performed by similar Components residing elsewhere.

In block 802, the 3D image update module 312 accesses a composite image (from composite image module 306). In block 804, the 3D image update module 312 accesses an x-ray image of the teeth of the patient 116. In block 806, the 3D image update module 312 aligns the x-ray image to the composite image. In block 808, the 3D image update module 312 updates the composite image based on the x-ray image.

Figure 9:
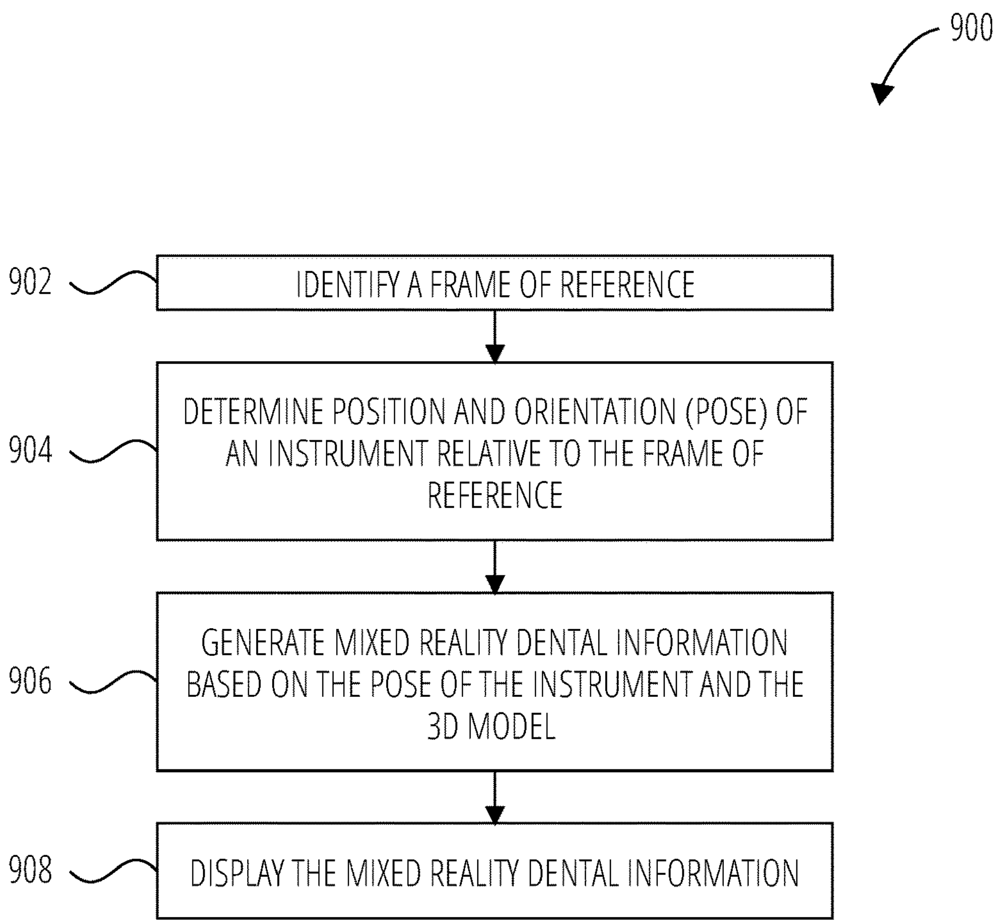
FIG. 9 illustrates a method for displaying mixed reality information in accordance with one example embodiment.

FIG. 9 illustrates a method 900 for displaying mixed reality information in accordance with one example embodiment. Operations in the method 900 may be performed by the dental instrument guidance system 512, using Components (e.g., modules, engines) described above with respect to FIG. 4 and FIG. 5. Accordingly, the method 900 is described by way of example with reference to the dental instrument guidance system 512. However, it shall be appreciated that at least some of the operations of the method 900 may be deployed on various other hardware configurations or be performed by similar Components residing elsewhere.

At block 902, the dental instrument guidance system 512 identifies a frame of reference by detecting the location of the reference object 416. At block 904, the mixed reality dental application 212 determines a position and orientation (pose) of the dental instrument 418 relative to the reference object 114. At block 906, the mixed reality dental application 212 generates augment reality dental information (e.g., digital information that is superimposed on a live view or a real-time display of the teeth of the patient 116). The AR dental information is based on the pose of the dental instrument 418 relative to the 3D model. At block 908, the mixed reality dental application 212 displays the augmented reality dental information in the display 202.

Figure 10:
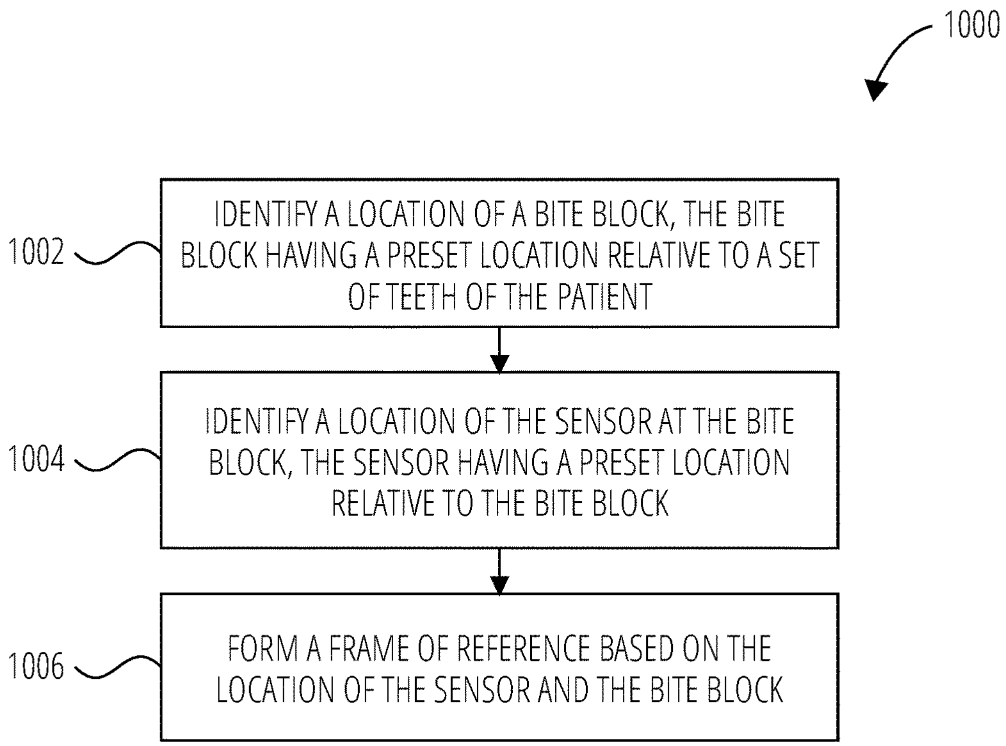
FIG. 10 illustrates a method for forming a frame of reference in accordance with one example embodiment.

FIG. 10 illustrates a method 1000 for forming a frame of reference in accordance with one example embodiment. Operations in the method 1000 may be performed by the bite block module 506, using Components (e.g., modules, engines) described above with respect to FIG. 5. Accordingly, the method 1000 is described by way of example with reference to the bite block module 506. However, it shall be appreciated that at least some of the operations of the method 1000 may be deployed on various other hardware configurations or be performed by similar Components residing elsewhere.

In block 1002, the bite block module 506 identifies a location of a bite block. The bite block has a preset location relative to a set of teeth of the patient. In block 1004, the bite block module 506 identifies a location of the sensor at the bite block. The sensor has a preset location relative to the bite block. In block 1006, the bite block module 506 forms/identifies a frame of reference based on the location of the sensor and the bite block.

Figure 11:
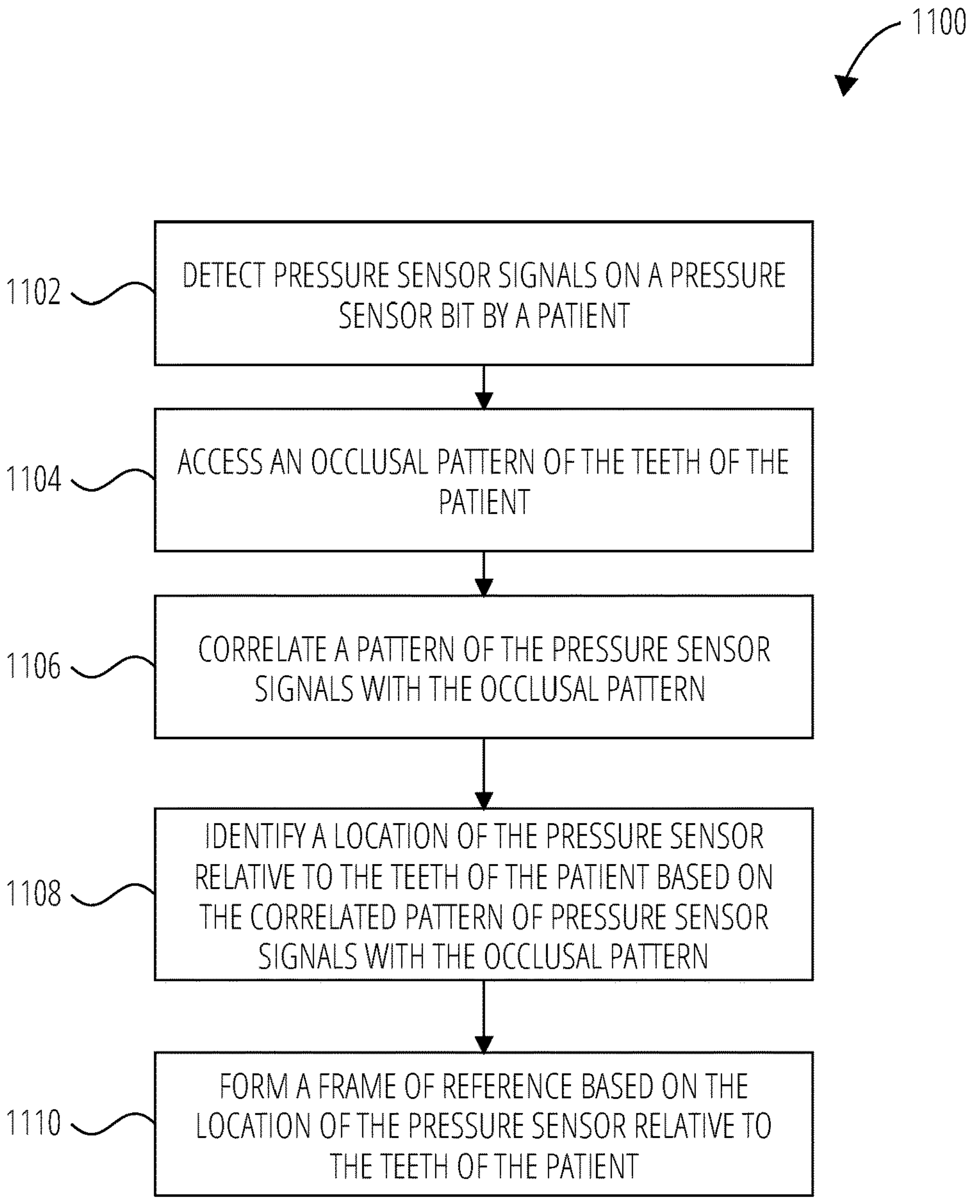
FIG. 11 illustrates a method for forming a frame of reference in accordance with another example embodiment.

FIG. 11 illustrates a method 1100 for forming a frame of reference in accordance with another example embodiment. Operations in the method 1100 may be performed by the pressure sensor module 508, using Components (e.g., modules, engines) described above with respect to FIG. 5. Accordingly, the method 1100 is described by way of example with reference to the pressure sensor module 508. However, it shall be appreciated that at least some of the operations of the method 1100 may be deployed on various other hardware configurations or be performed by similar Components residing elsewhere.

In block 1102, the pressure sensor module 508 detects pressure sensor signals on a pressure sensor bit by a patient. In block 1104, the pressure sensor module 508 accesses an occlusal pattern of the teeth of the patient. In block 1106, the pressure sensor module 508 correlates a pattern of the pressure sensor signals with the occlusal pattern. In block 1108, the pressure sensor module 508 identifies a location of the pressure sensor relative to the teeth of the patient based on the correlated pattern of pressure sensor signals with the occlusal pattern. In block 1110, the pressure sensor module 508 forms/identifies a frame of reference based on the location of the pressure sensor relative to the teeth of the patient.

Figure 12:
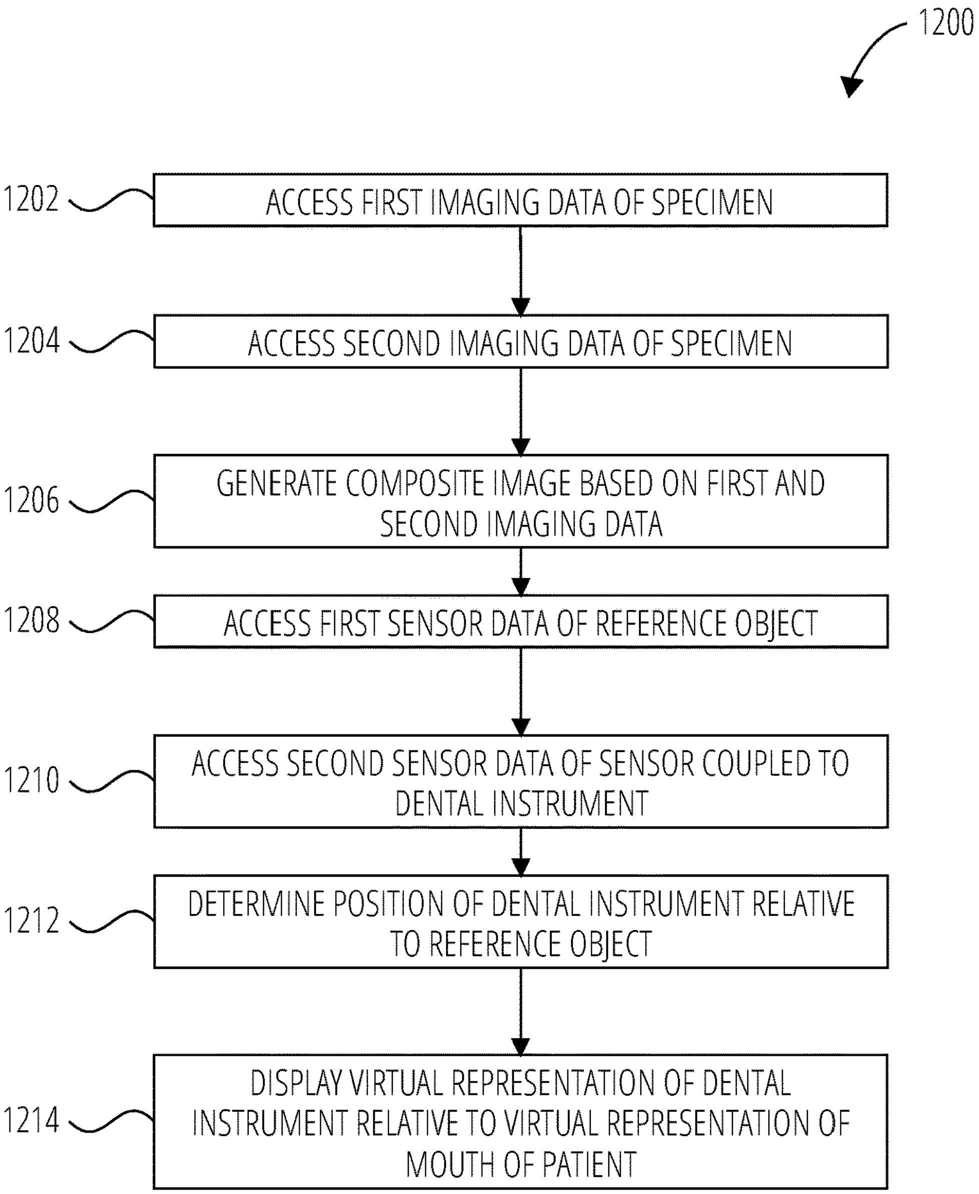
FIG. 12 illustrates a method for displaying a virtual representation in accordance with one example embodiment.

FIG. 12 illustrates a method 1200 for displaying a virtual representation in accordance with one example embodiment. Operations in the method 1200 may be performed by the imaging application 208 and guidance application 412, using Components (e.g., modules, engines) described above with respect to FIG. 2 and FIG. 4. Accordingly, the method 1200 is described by way of example with reference to the imaging application 208 and guidance application 412.

However, it shall be appreciated that at least some of the operations of the method 1200 may be deployed on various other hardware configurations or be performed by similar Components residing elsewhere.

In block 1202, the imaging application 208 accesses first imaging data of a specimen using a first sensor device, the first imaging data comprising volumetric data. In block 1204, imaging application 208 accesses second imaging data of the specimen using a second sensor device, the second imaging data comprising surface data. In block 1206, the imaging application 208 generates a composite image based on the first and second imaging data, the composite image indicating the volumetric data and the surface data of the specimen. In block 1208, the guidance application 412 accesses first sensor data of a reference object resting in a mouth of a patient, the reference object being at a predefined position relative to the mouth of the patient. In block 1210, the guidance application 412 accesses second sensor data of a sensor coupled to a dental instrument. In block 1212, the guidance application 412 determines a position of the dental instrument relative to the reference object based on the first and second sensor data. In block 1214, guidance application 412 displays a virtual representation of the dental instrument relative to a virtual representation of the mouth of the patient based on the position of the dental instrument relative to the reference object.

Figure 13:
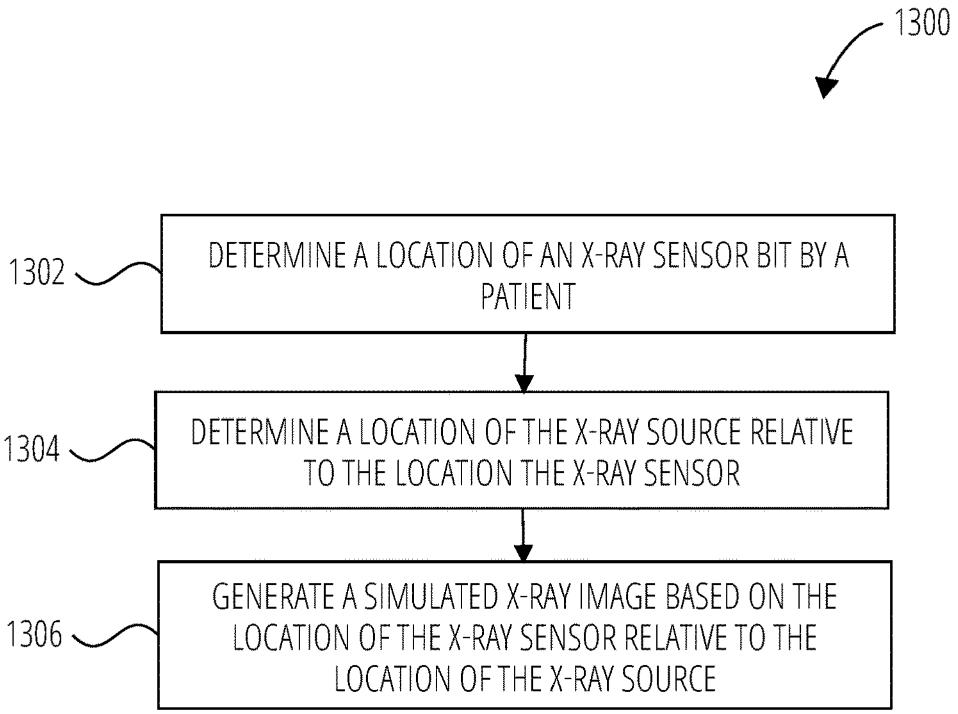
FIG. 13 illustrates a method for generating a simulated x-ray image in accordance with one example embodiment.

FIG. 13 illustrates a method 1300 for generating a simulated x-ray image in accordance with one example embodiment. Operations in the method 1300 may be performed by the imaging application 208 and guidance application 412, using Components (e.g., modules, engines) described above with respect to FIG. 2 and FIG. 4. Accordingly, the method 1300 is described by way of example with reference to the imaging application 208 and guidance application 412. However, it shall be appreciated that at least some of the operations of the method 1200 may be deployed on various other hardware configurations or be performed by similar Components residing elsewhere.

In block 1302, the x-ray guidance system 514 determines a location of an x-ray sensor bit by a patient. In block 1304, the x-ray guidance system 514 determines a location of the x-ray source relative to the location the x-ray sensor. In block 1306, the x-ray guidance system 514 generates a simulated x-ray image based on the location of the x-ray sensor relative to the location of the x-ray source.

Figure 14:
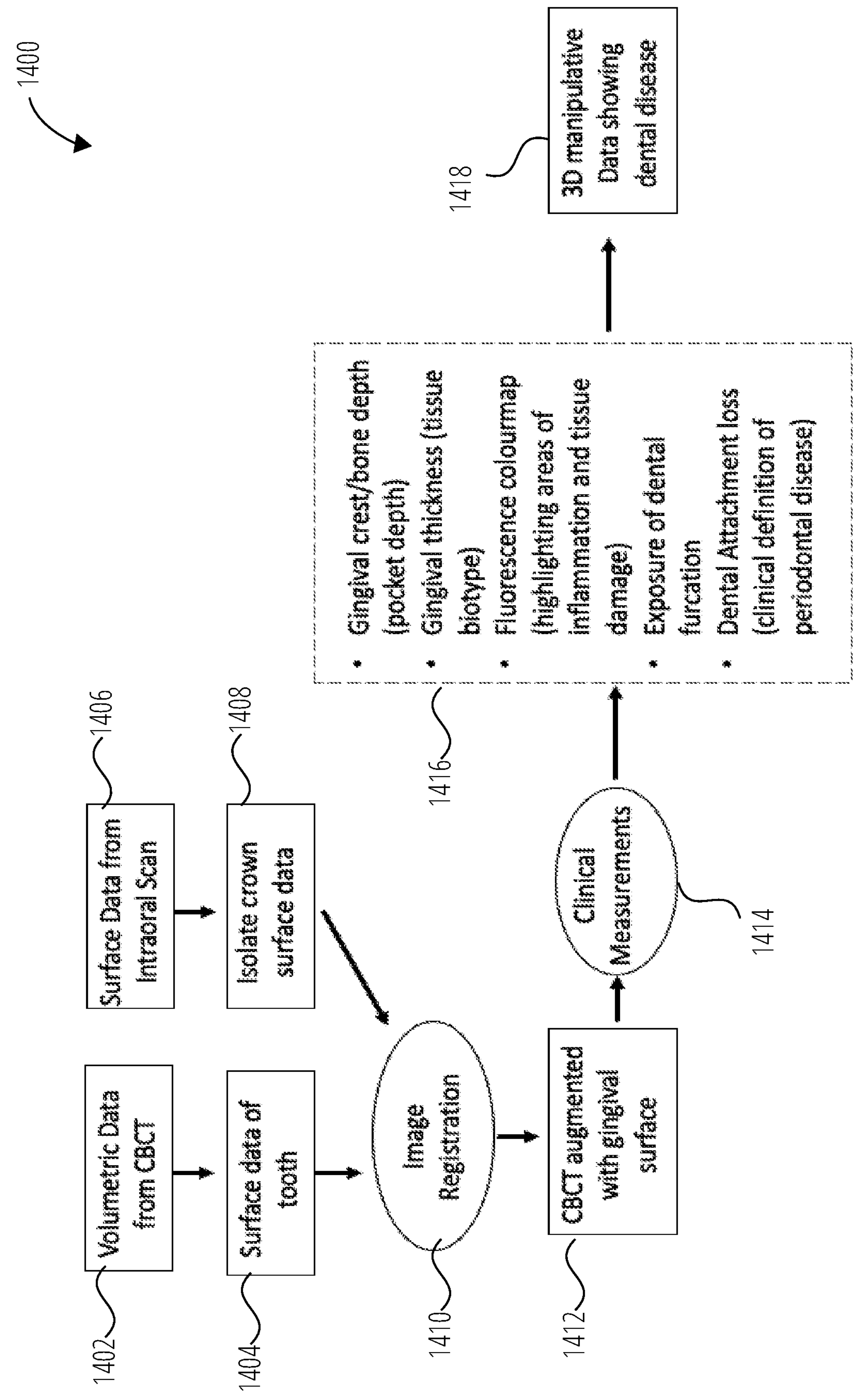
FIG. 14 illustrates an example process of an imaging system in accordance with one example embodiment.

FIG. 14 illustrates an example process of an imaging system in accordance with one example embodiment. The volumetric data from CBCT 1402 provides surface data of tooth 1404. The surface data from intraoral scan 1406 is used to identify crown surface data 1408. At image registration 1410, both the surface data of tooth 1404 and crown surface data 1408 are registered to generate a composite image (image registration 1410). The composite image indicates CBCT augmented with gingival surface 1412 that can be used for clinical measurements 1414. Examples of clinical measurements 1416 include pocket depth, tissue biotype, and areas of inflammation. Data from the clinical measurements 1414 can be used to generate 3D manipulative data showing dental disease 1418.

Figure 15:
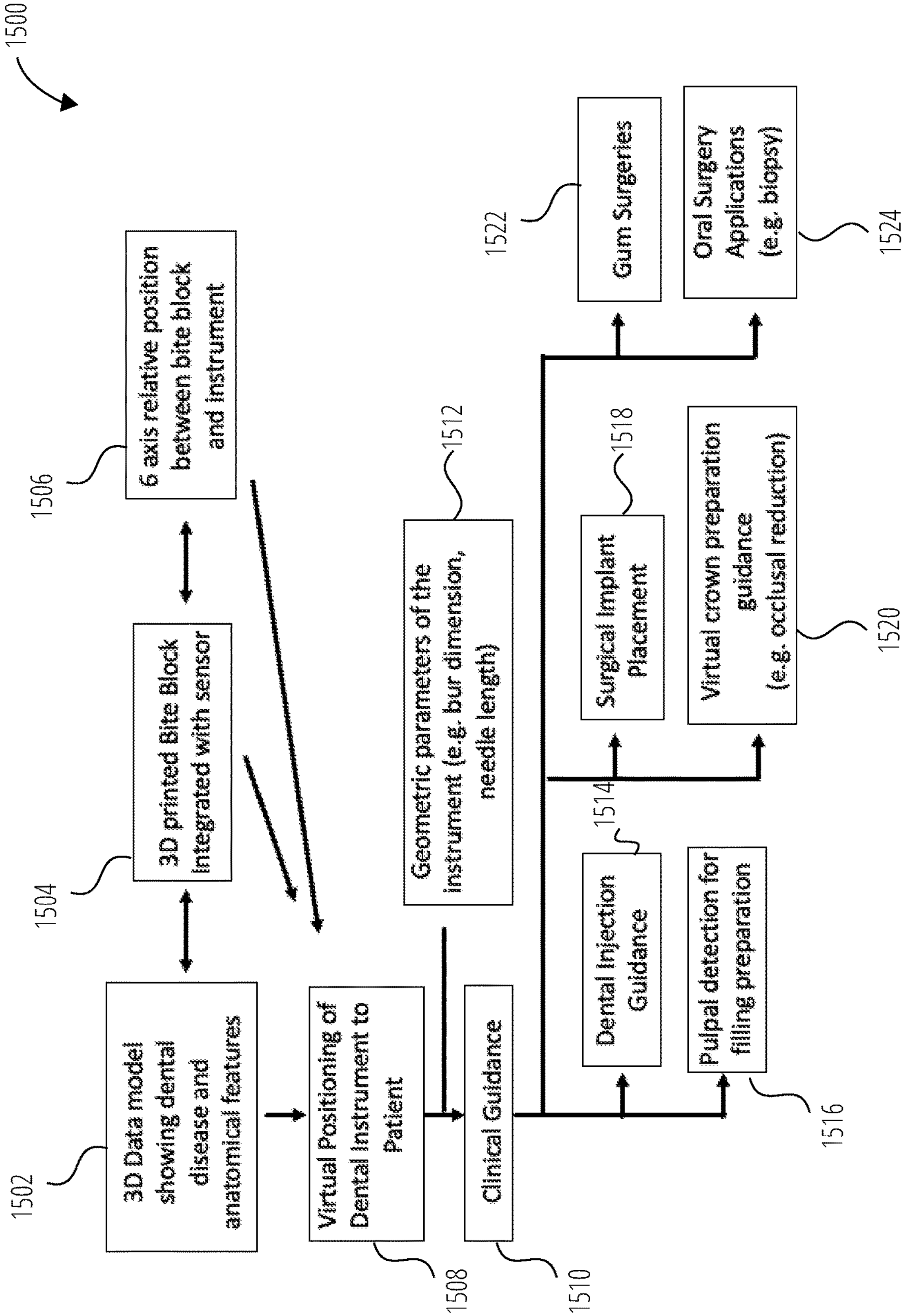
FIG. 15 illustrates an example process of a guidance system in accordance with one example embodiment.

FIG. 15 illustrates an example process of a guidance system in accordance with one example embodiment. In block 1508, the virtual positioning of the x-ray source 108 relative to the patient 116 is based on a reference object 114 (e.g., 3D printed custom bite block with sensors) at block 1504 and the relative position between the reference object 114 and the x-ray source 108 at block 1506. The virtual positioning of the x-ray source 108 relative to the patient 116 is also based on the 3D data model showing dental disease and anatomical features at block 1502.

The geometric parameters of the x-ray source 108 at block 1512 are used along with the virtual positioning of the x-ray source 108 for clinical guidance at block 1510. Examples of clinical guidance include dental injection guidance at block 1514, surgical implant placement at block 1518, and gum surgeries at block 1522, pulpal detection for filling preparation at block 1516, virtual crown preparation guidance at block 1520, and oral surgery applications at block 1524.

Figure 16:
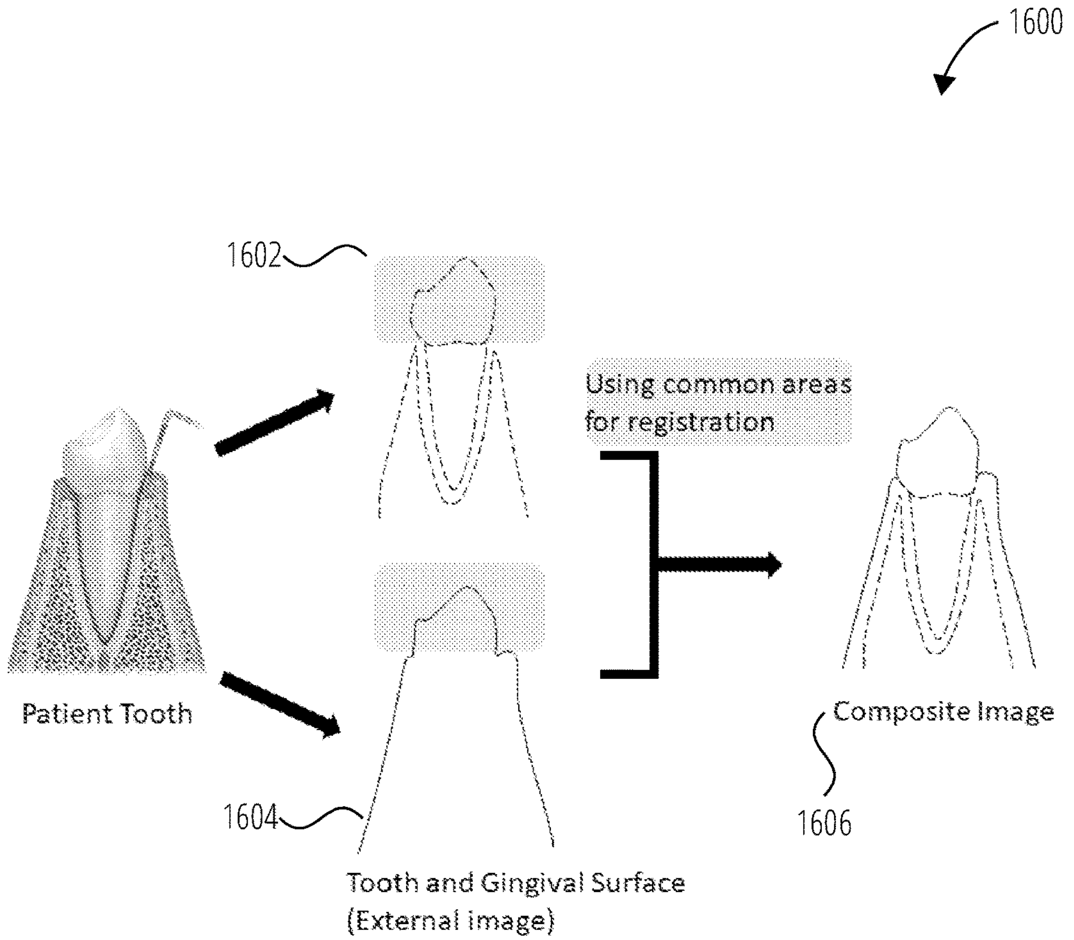
FIG. 16 illustrates an example of combining a first and second dental imaging data to generate a composite image in accordance with one example embodiment.

FIG. 16 illustrates an example 1600 of combining a first and second dental imaging data to generate a composite image in accordance with one example embodiment. The soft tissue image 1602 and the tooth surface image 1604 are combined into a composite image 1606.

Figure 17:
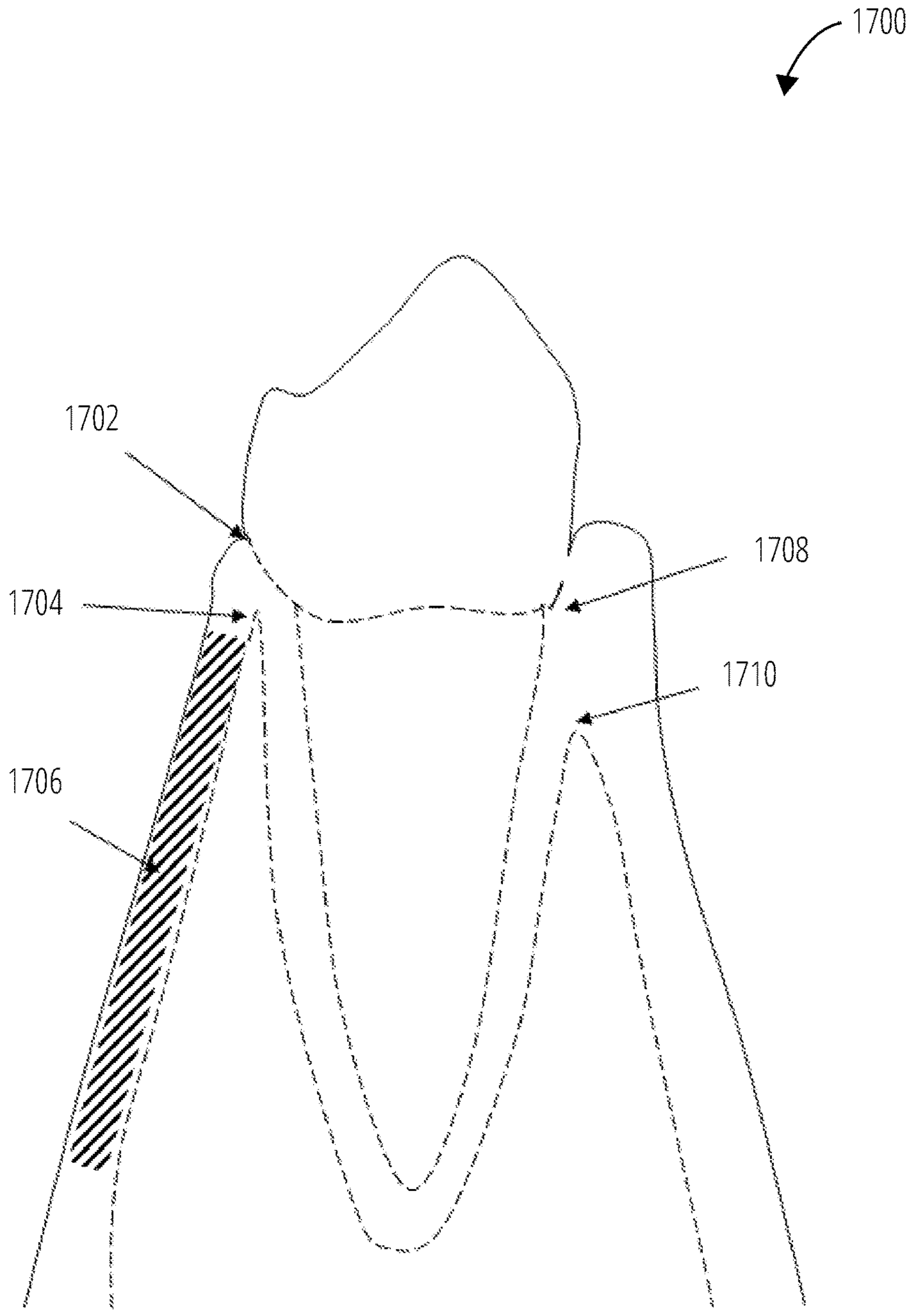
FIG. 17 illustrates a cross-section of a tooth in accordance with one example embodiment.

FIG. 17 illustrates a cross-section 1700 of a composite image of a tooth in accordance with one example embodiment. Examples of periodontal calculations performed by the imaging application 208 include:

- Probing Depth (distance between top contact between tooth/gum and crest of bone-distance between point 1702 and point 1704)
- Attachment Loss (periodontitis) (approximate height difference between enamel/root junction and alveolar bone crest-distance between point 1708 and point 1710)
- Gingival Swelling (gingivitis) (probing depth+attachment loss-physiological pocket depth (about 2-3 mm))
- Gingival biotype (thick or thin) (thickness depth between gum and supporting bone based average thickness of area 1706).

Figure 18:
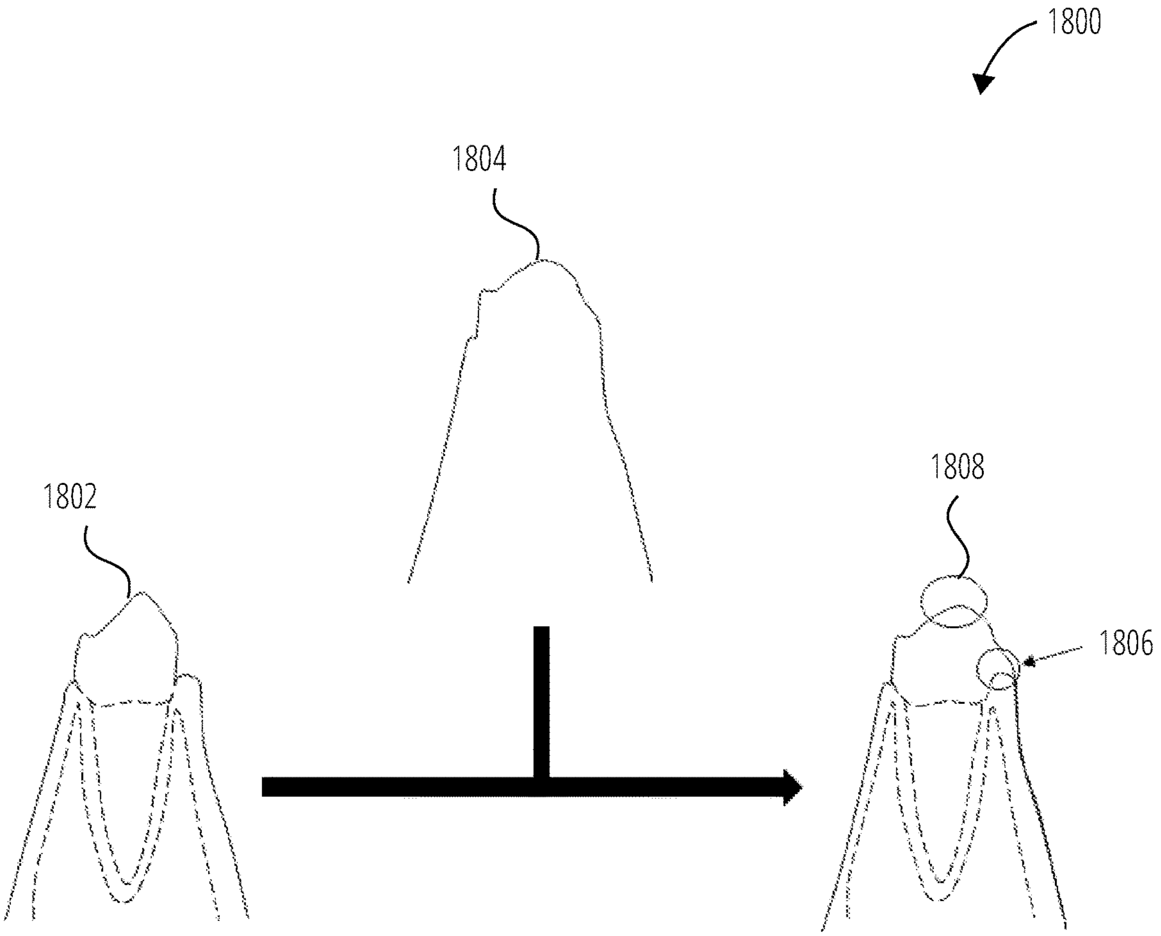
FIG. 18 illustrates a composite image of a cross-section of a tooth in accordance with one example embodiment.

FIG. 18 illustrates a composite image of a cross-section 1800 of a tooth in accordance with one example embodiment. cross-section 1802 illustrates an existing composite image. item 1804 illustrates a 3D surface from new patient scan. An area of surface addition 1806 illustrates an updated composite image that indicates the area of surface addition 1806, and area of surface wear 1808.

Figure 19:
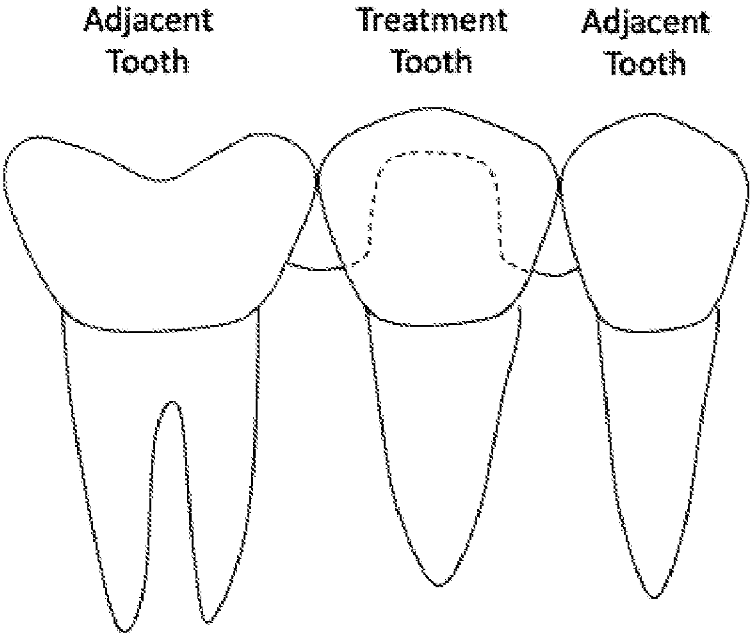
FIG. 19 illustrates a cross-section of a crown treatment tooth in accordance with one example embodiment.

FIG. 19 illustrates a cross-section of a crown treatment tooth in accordance with one example embodiment.

Figure 20:
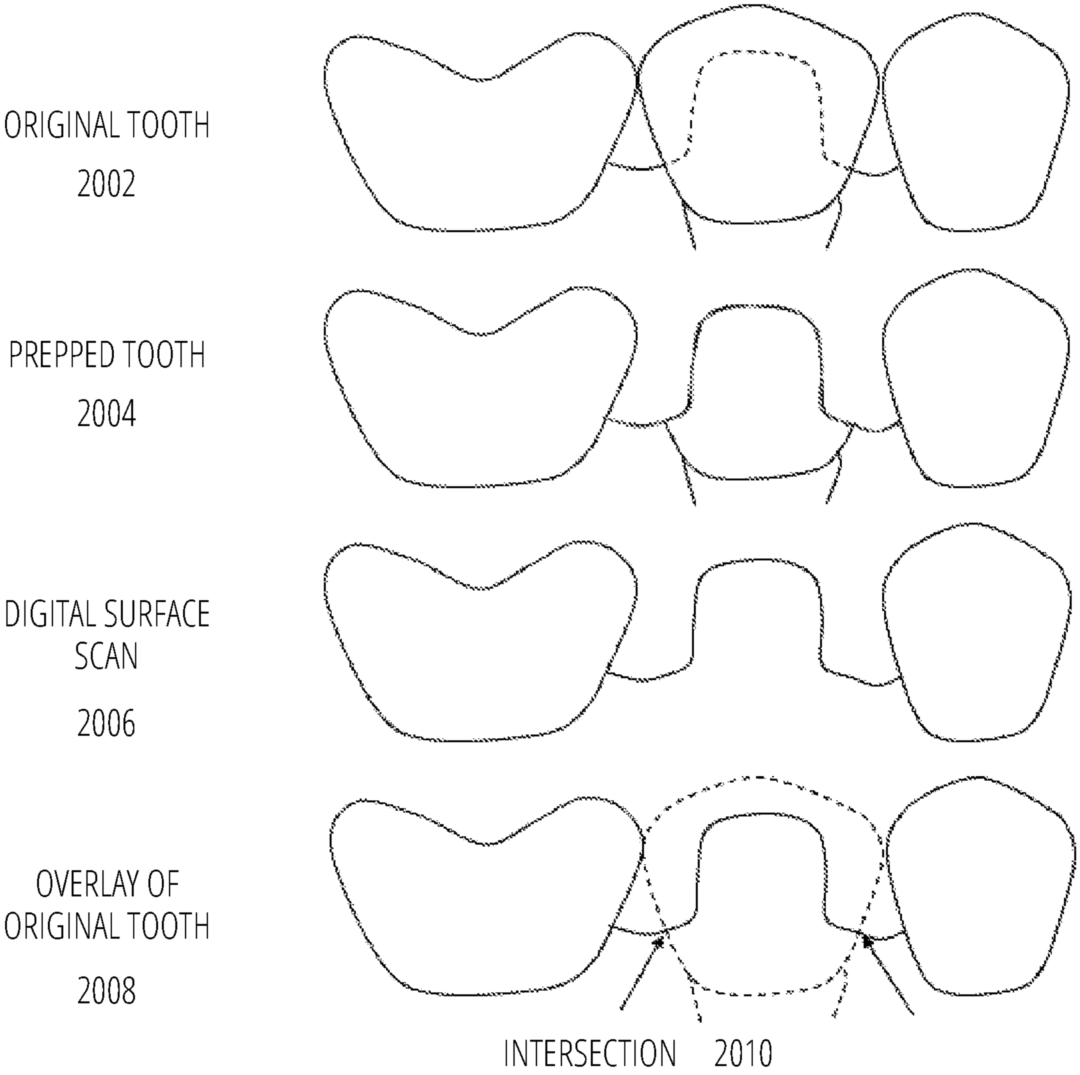
FIG. 20 illustrates a progression of a crown treatment tooth in accordance with one example embodiment.

FIG. 20 illustrates a progression of a crown treatment tooth in accordance with one example embodiment: an original tooth 2002, a prepped tooth 2004, a digital surface scan 2006, an overlay of original tooth 2008, and an intersection 2010.

Figure 21:
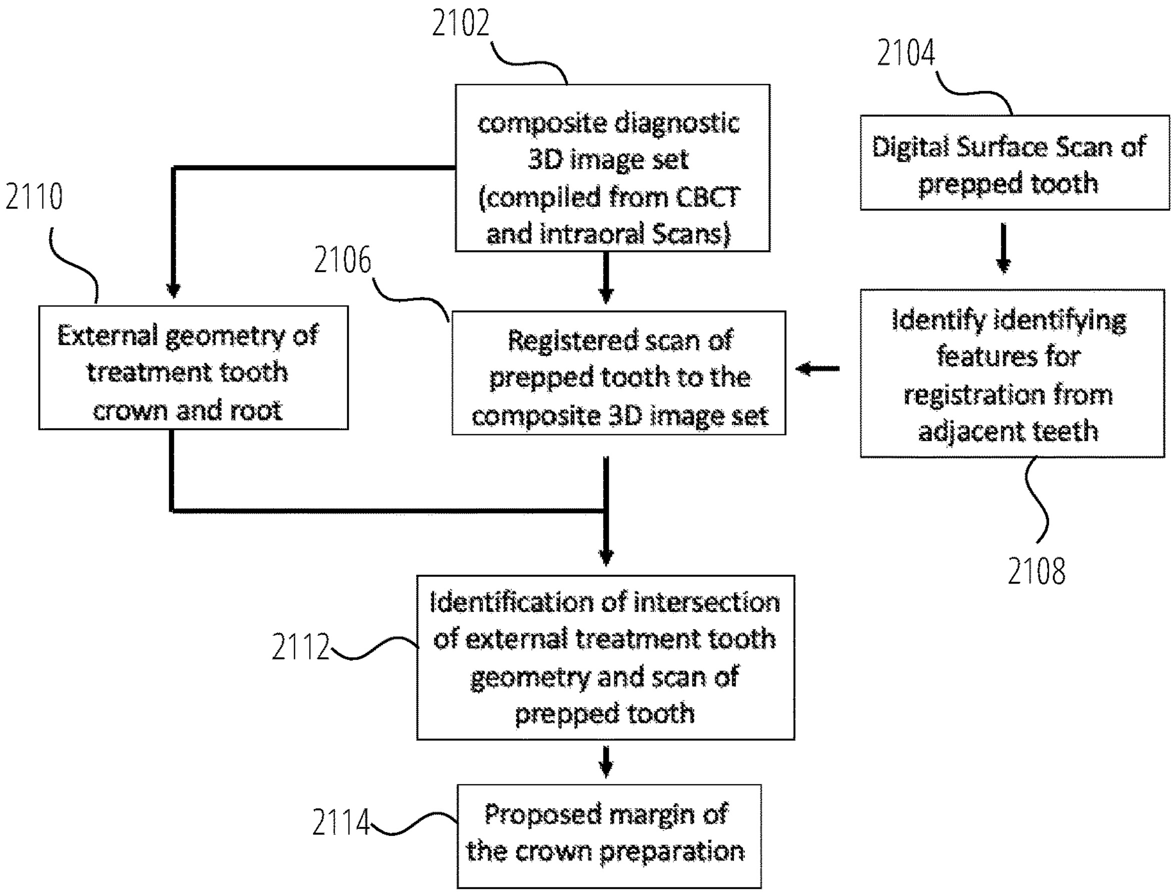
FIG. 21 illustrates an example process for generating a proposed margin of crown in accordance with one example embodiment.

FIG. 21 illustrates an example process for generating a proposed margin of crown in accordance with one example embodiment. At operation 2102, the composite image module 306 generates a composite diagnostic 3D image set compiled from CBCT and intraoral scans. The composite diagnostic 3D image set is used to identify external geometry of treatment of tooth crown and root at operation 2110. The composite diagnostic 3D image set is also used to register scan of prepped tooth to the composite 3D image set at operation 2106 using identified features from registration of adjacent teeth from operation 2108. Operation 2108 is performed using digital surface scan of the prepped tooth at operation 2104.

The registered scan of the prepped tooth and the external geometry of treatment tooth crown and root are used to identify intersection of external treatment tooth at operation 2112. The proposed margin of crown preparation is identified in operation 2114.

Figure 22:
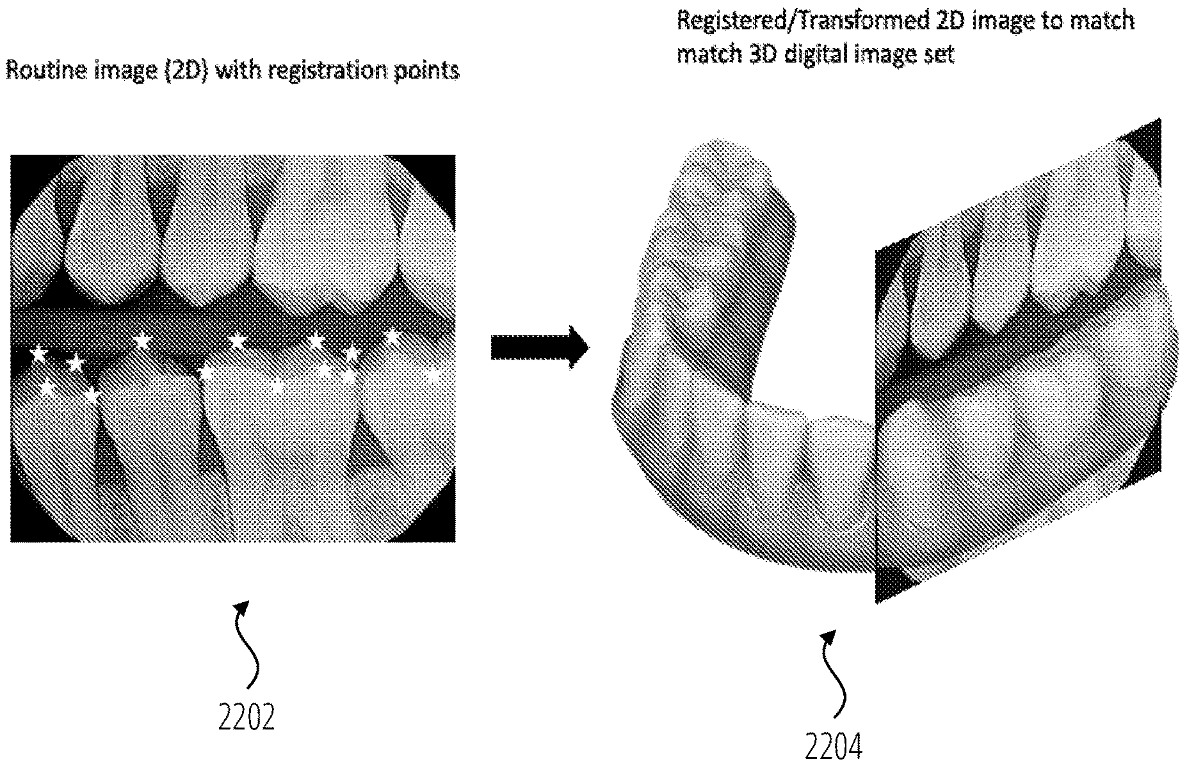
FIG. 22 illustrates an example operation of registering a 2D image to a 3D image in accordance with one embodiment.

FIG. 22 illustrates an example operation of registering a 2D image 2202 to a 3D image 2204 in accordance with one embodiment.

Figure 23:
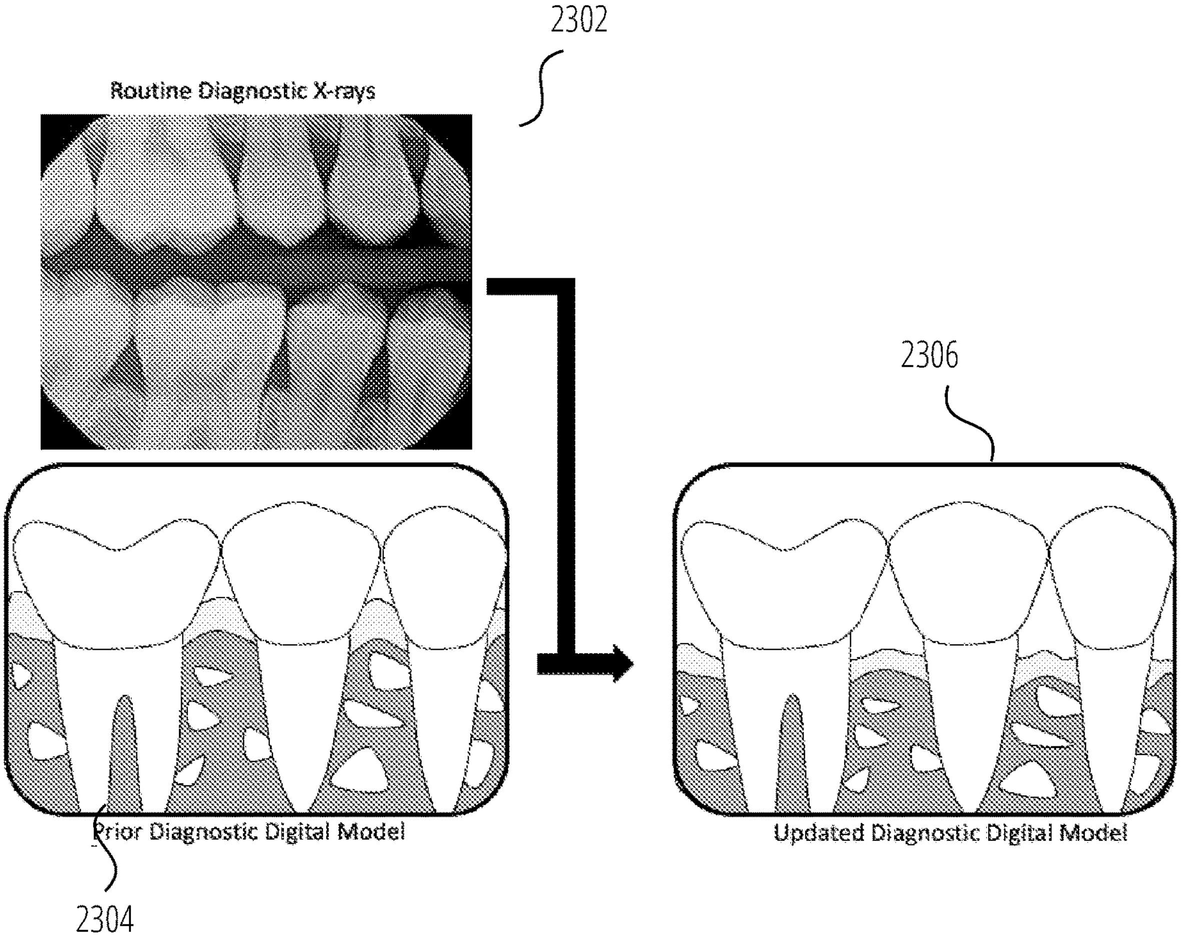
FIG. 23 illustrates an example operation of updating a digital model in accordance with one example embodiment.

FIG. 23 illustrates an example operation of updating a digital model in accordance with one example embodiment. The x-ray image 2302 is registered/compared with prior digital model 2304 to generate updated digital model 2306.

Figure 24:
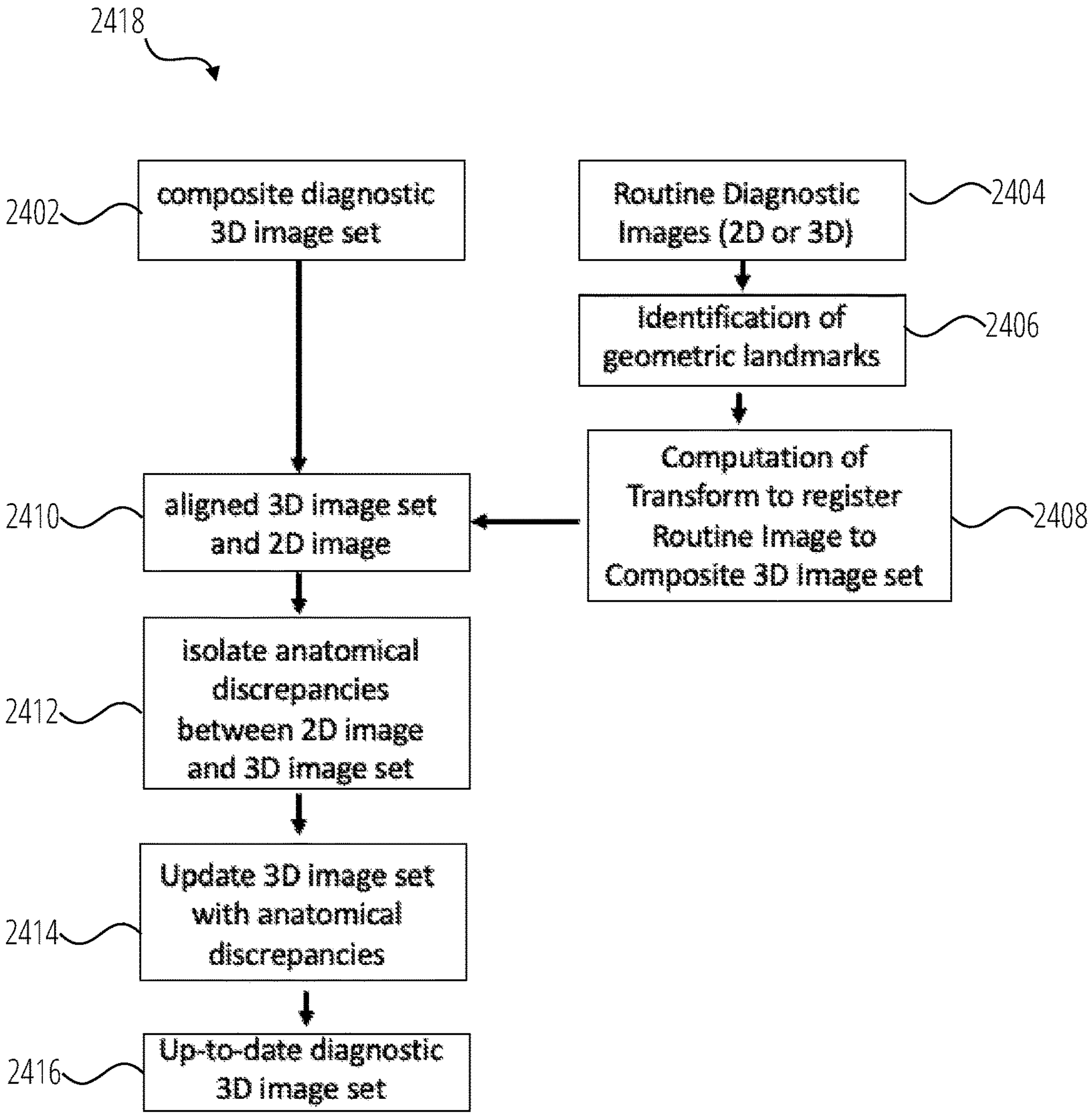
FIG. 24 is flow diagram illustrating a process for updating a digital model in accordance with one example embodiment.

FIG. 24 is flow diagram illustrating a process 2418 for updating a digital model in accordance with one example embodiment. At operation 2402, the imaging application 208 accesses a composite diagnostic 3D image set. At operation 2404, the imaging application 208 retrieves routine diagnostic images. At operation 2406, the imaging application 208 identifies geometric landmarks in the diagnostic images. At operation 2408, the imaging application 208 performs computation of transform to register routing image to composite 3D image set.

At operation 2410, the imaging application 208 aligns the 3D image set from operation 2402 and 2D image from operation 2408. At operation 2412, the imaging application 208 isolates anatomical discrepancies between 2D image and 3D image set. At operation 2412, the imaging application 208 updates the 3D image set with anatomical discrepancies. At operation 2416, the imaging application 208 generates up-to-date diagnostic 3D image set.

Figure 25:
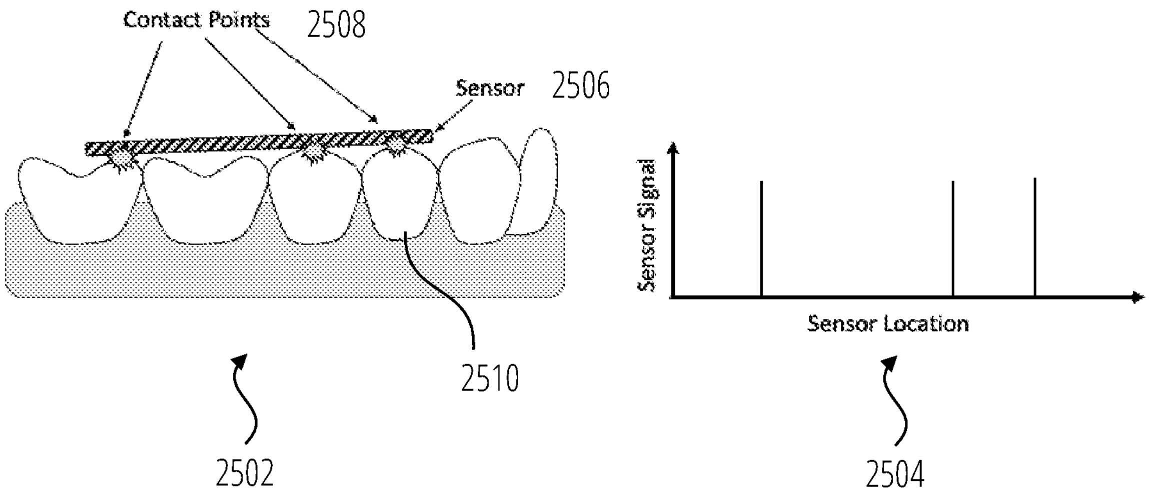
FIG. 25 is a block diagram illustrating a reference object including a pressure sensor in accordance with one example embodiment.

FIG. 25 is a block diagram illustrating a reference object including a pressure sensor 2506 in accordance with one example embodiment. The cross-section view 2502 illustrates contact points 2508 between the pressure sensor 2506 and the teeth 2510. The graph 2504 illustrates sensor signals corresponding to the locations on the pressure sensor 2506.

Figure 26:
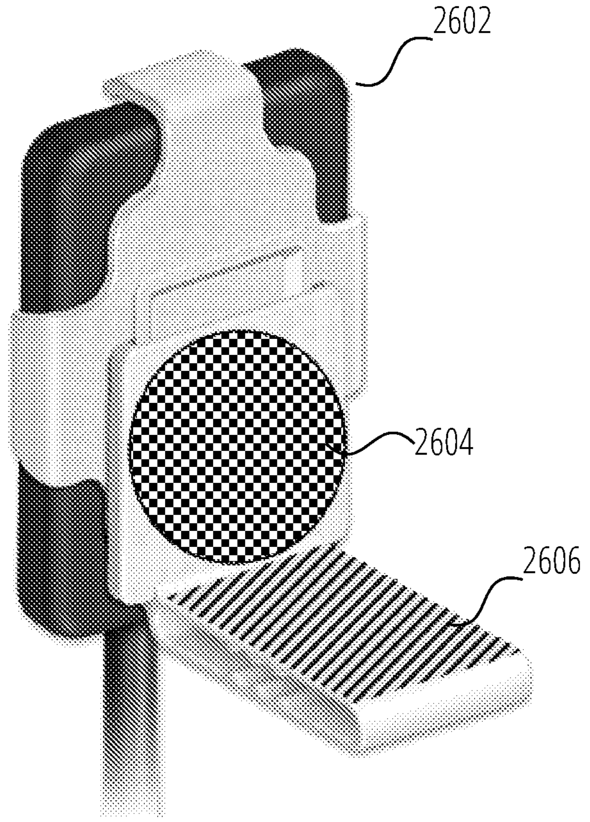
FIG. 26 illustrates an x-ray sensor in accordance with one example embodiment.

FIG. 26 illustrates an x-ray sensor 2602 in accordance with one example embodiment. The x-ray sensor 2602 is coupled to x-ray position sensor 2604 and pressure sensor array 2606 at predefined locations.

Figure 27:
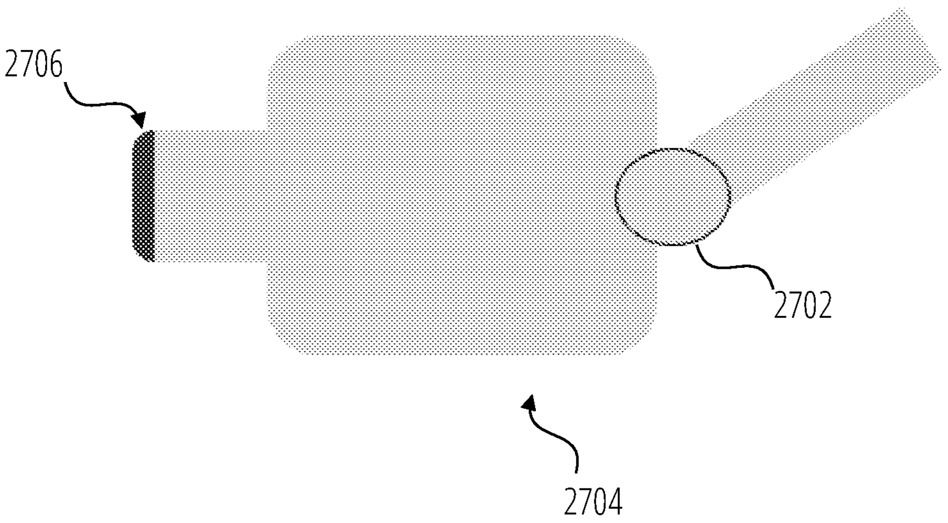
FIG. 27 illustrates an x-ray source in accordance with one example embodiment.

FIG. 27 illustrates an x-ray source in accordance with one example embodiment. The x-ray source 2704 includes a x-ray source positional sensor 2706 and motorized articulating arm 2702.

Figure 28:
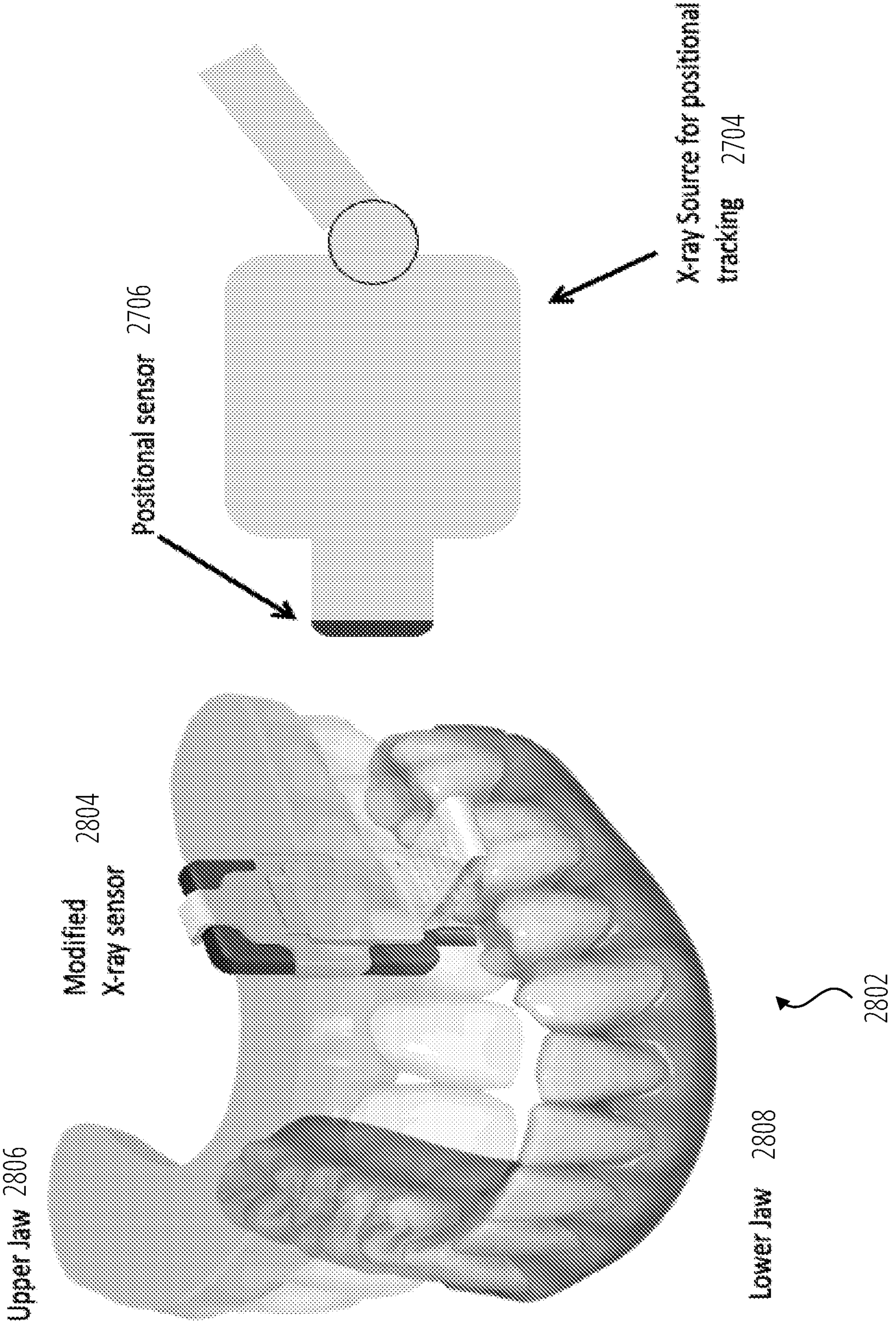
FIG. 28 illustrates an operation configuration of an x-ray sensor in accordance with one example embodiment.

FIG. 28 illustrates an operation configuration of an x-ray sensor in accordance with one example embodiment. The view 2802 illustrates the x-ray sensor 2804 being placed between the upper jaw 2806 and lower jaw 2808. The x-ray source 2704 is directed at the x-ray sensor 2804.

Figure 29:
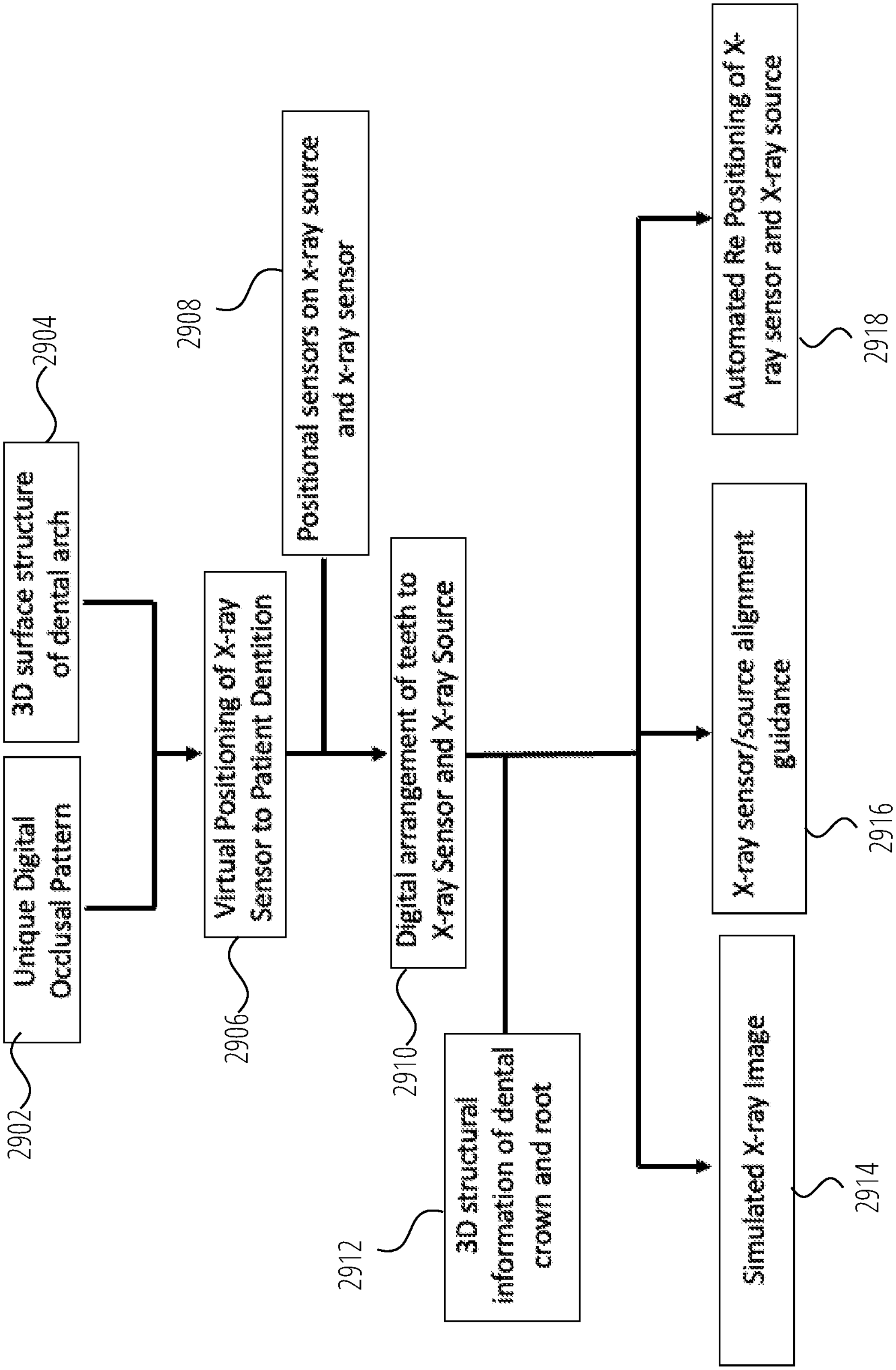
FIG. 29 is a flow diagram illustrating a process for generating a simulated x-ray image and providing guidance in accordance with one example embodiment.

FIG. 29 is a flow diagram illustrating a process for generating a simulated x-ray image and providing guidance in accordance with one example embodiment. At block 2902, the imaging system 118 retrieves the unique digital pattern. At block 2904, the imaging system 118 identifies the 3D surface structure of the dental arch. At block 2906, the guidance system 102 identifies the virtual positional of the x-ray sensor 120 to the patient 116's teeth. At block 2908, the guidance system 102 identifies positional sensors on the x-ray source 108 and the x-ray sensor 120. At block 2910, the imaging system 118 identifies the digital arrangement of teeth relative to the x-ray sensor 120 and the x-ray source 108. At block 2912, the imaging system 118 determines the 3D structural information of dental crown and root. At block 2914, the imaging system 118 generates a simulated x-ray image. At block 2916, the guidance system 102 provides x-ray sensor 120/x-ray source 108 alignment guidance. At block 2918, the guidance system 102 can also automatically re-position the x-ray sensor 120 and the x-ray source 108.

Figure 30:
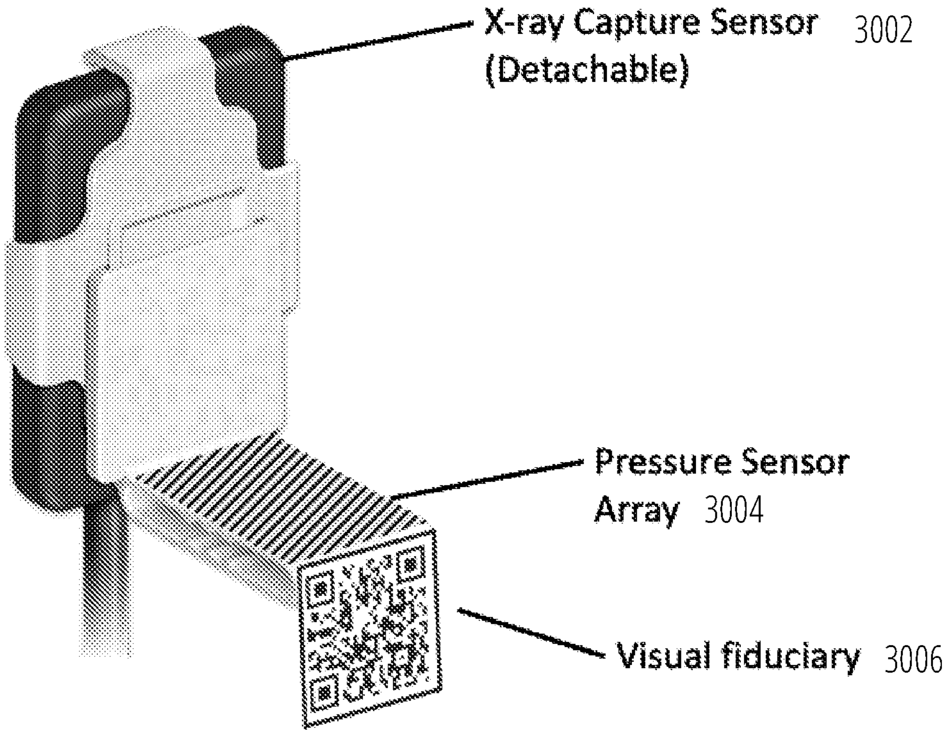
FIG. 30 illustrates an x-ray sensor in accordance with another example embodiment.

FIG. 30 illustrates an x-ray sensor 3002 in accordance with another example embodiment. The x-ray sensor 3002 includes a pressure sensor array 3004 and a visual fiduciary 3006 (e.g., QR code).

Figure 31:
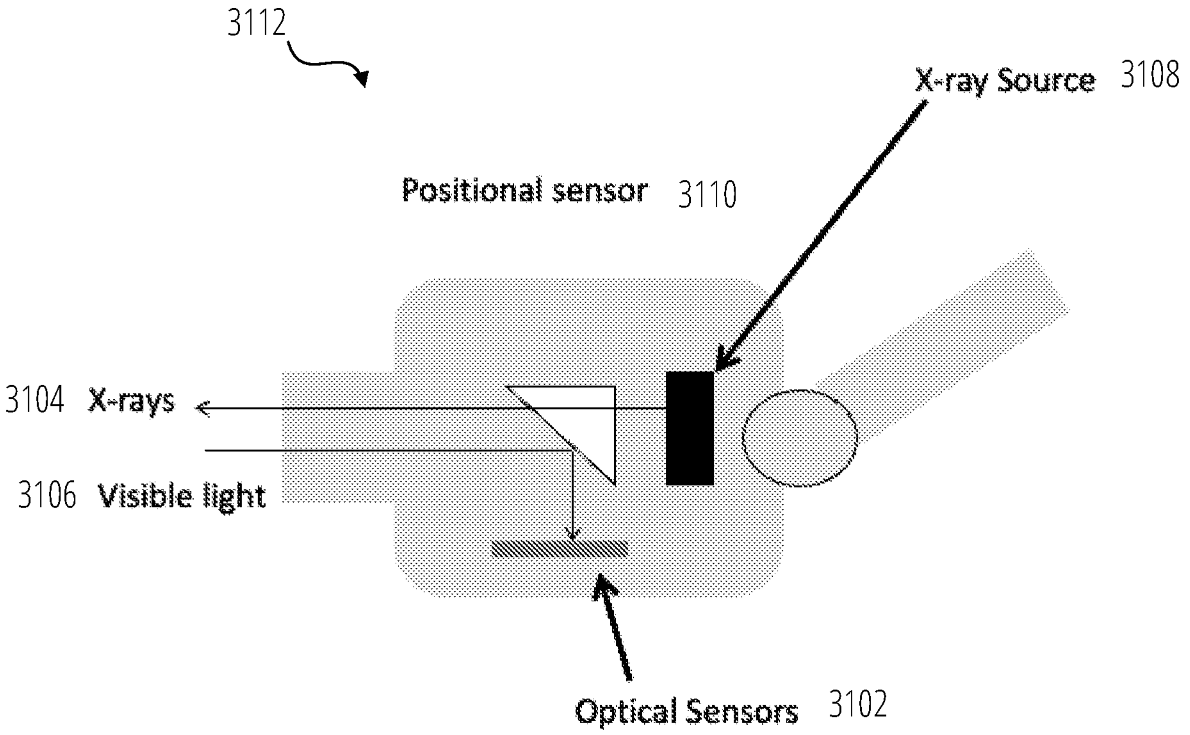
FIG. 31 illustrates an x-ray source in accordance with another example embodiment.

FIG. 31 illustrates an x-ray device 3112 in accordance with another example embodiment. The x-ray device 3112 includes an x-ray source 3108, a positional sensor 3110, an optical sensors 3102. The x-ray source 3108 generates x-rays 3104. The optical sensors 3102 detects visible light 3106.

Figure 32:
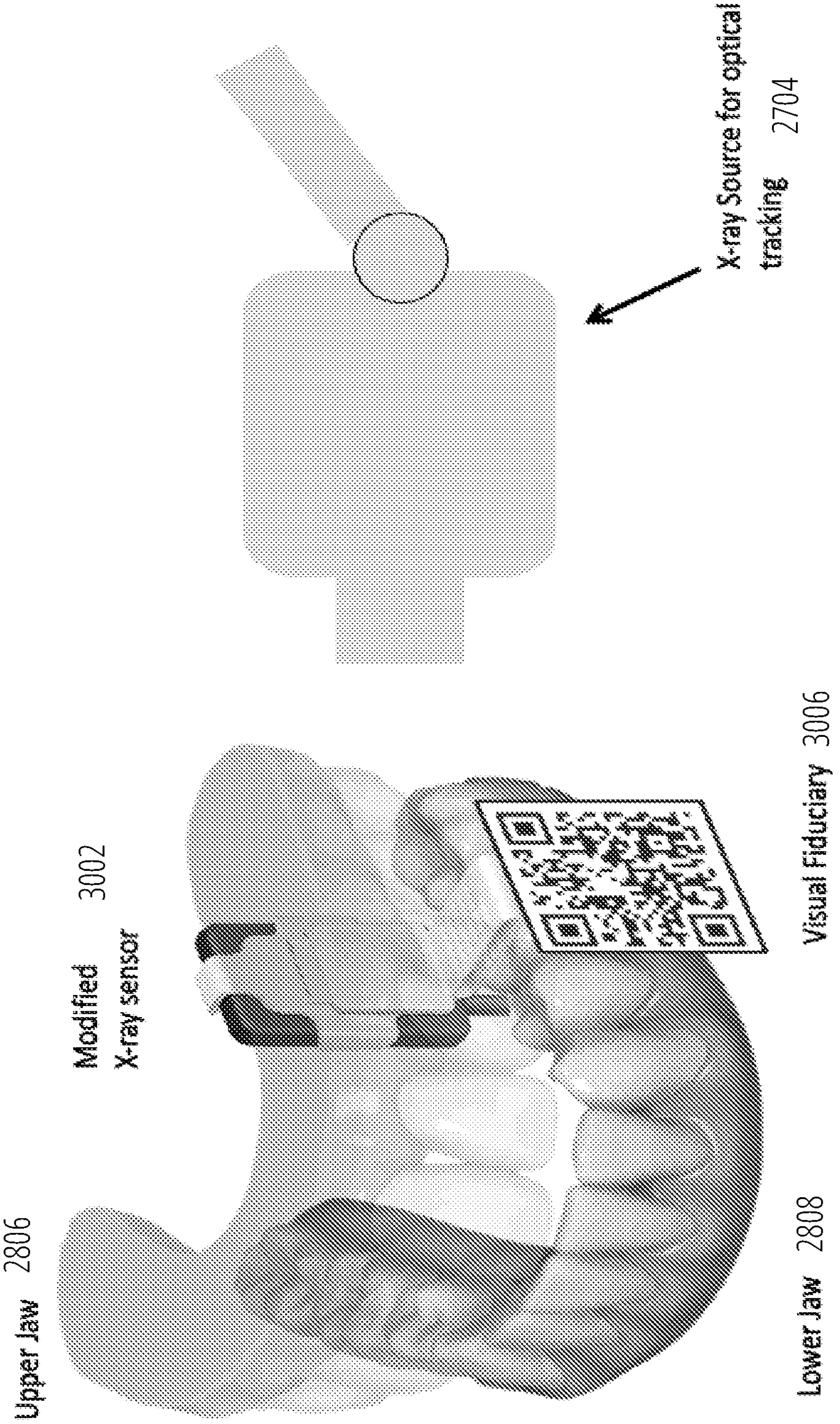
FIG. 32 illustrates an operation configuration of an x-ray sensor in accordance with another example embodiment.

FIG. 32 illustrates an operation configuration of an x-ray sensor in accordance with another example embodiment. The x-ray source 2704 is directed to the visual fiduciary 3006 of the x-ray sensor 3002.

Figure 33:
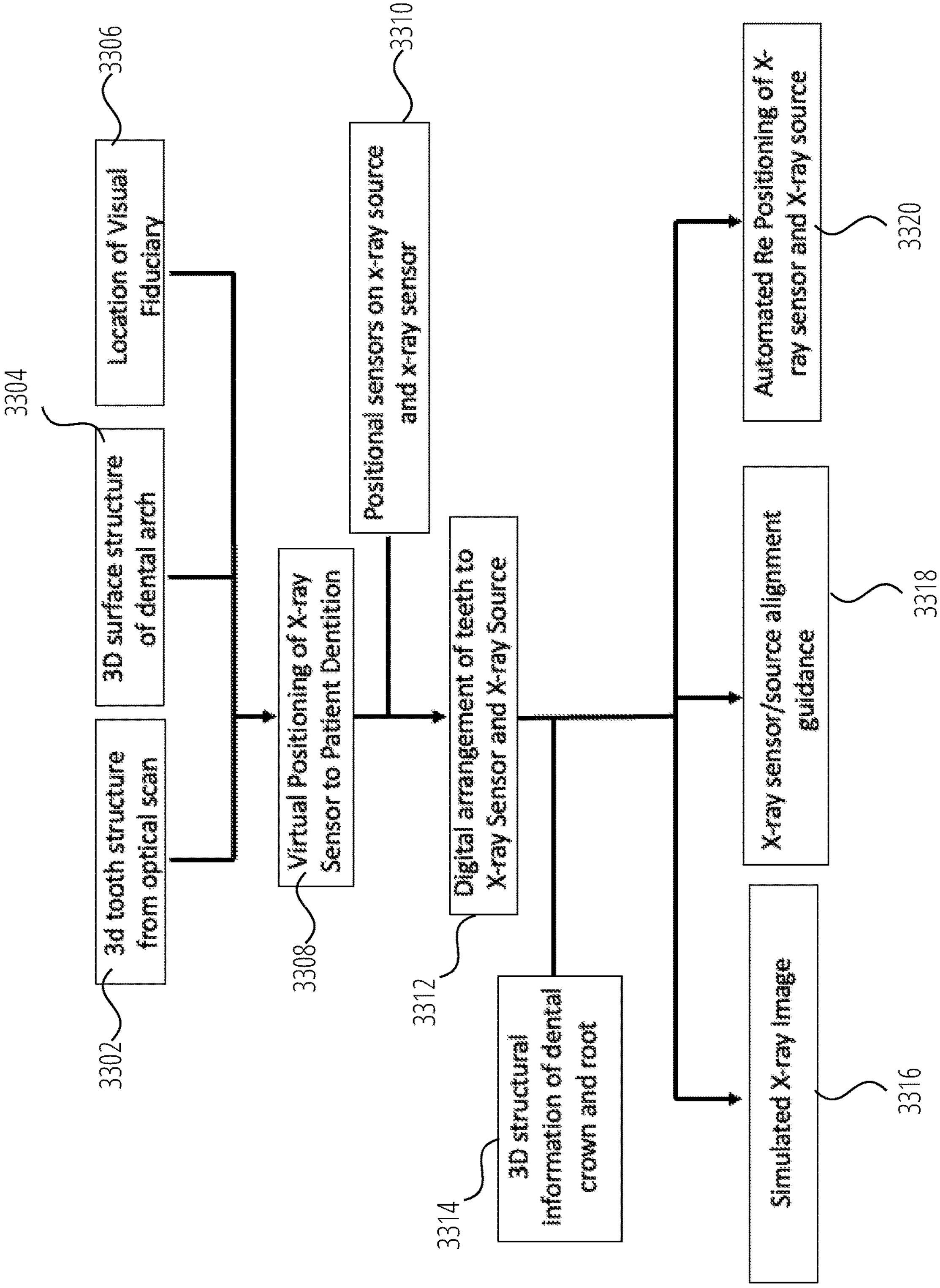
FIG. 33 is a flow diagram illustrating a process for generating a simulated x-ray image and providing guidance in accordance with one example embodiment.

FIG. 33 is a flow diagram illustrating a process for generating a simulated x-ray image and providing guidance in accordance with one example embodiment. At block 3302, the imaging system 118 accesses the 3D tooth structure from optical scan. At block 3304, the imaging system 118 identifies the 3D surface structure of dental arch. At block 3306, the imaging system 118 identifies the location of visual fiduciary.

At block 3308, the imaging system 118 generates a virtual positioning of the x-ray sensor 120 relative to the patient 116's teeth. The imaging system 118 accesses, at block 3310, the x-ray positional data on the x-ray source 108 and the x-ray sensor 120. At block 3312, the imaging system 118 generates a digital arrangement of teeth relative to the x-ray sensor 120 and x-ray source 108. At block 3314, the imaging system 118 accesses the 3D structural information of dental crown and root. The imaging system 118 uses the data from block 3314 and block 3312 to generate simulated x-ray image at block 3316. The guidance system 102 uses the data from block 3314 and block 3314 to provide guidance for the x-ray sensor 120 and the x-ray source 108 alignment at block 3318. The guidance system 102 uses the data from block 3314 and block 3314 to automatically reposition the location of the x-ray source 108 and the x-ray sensor 120.

Figure 34:
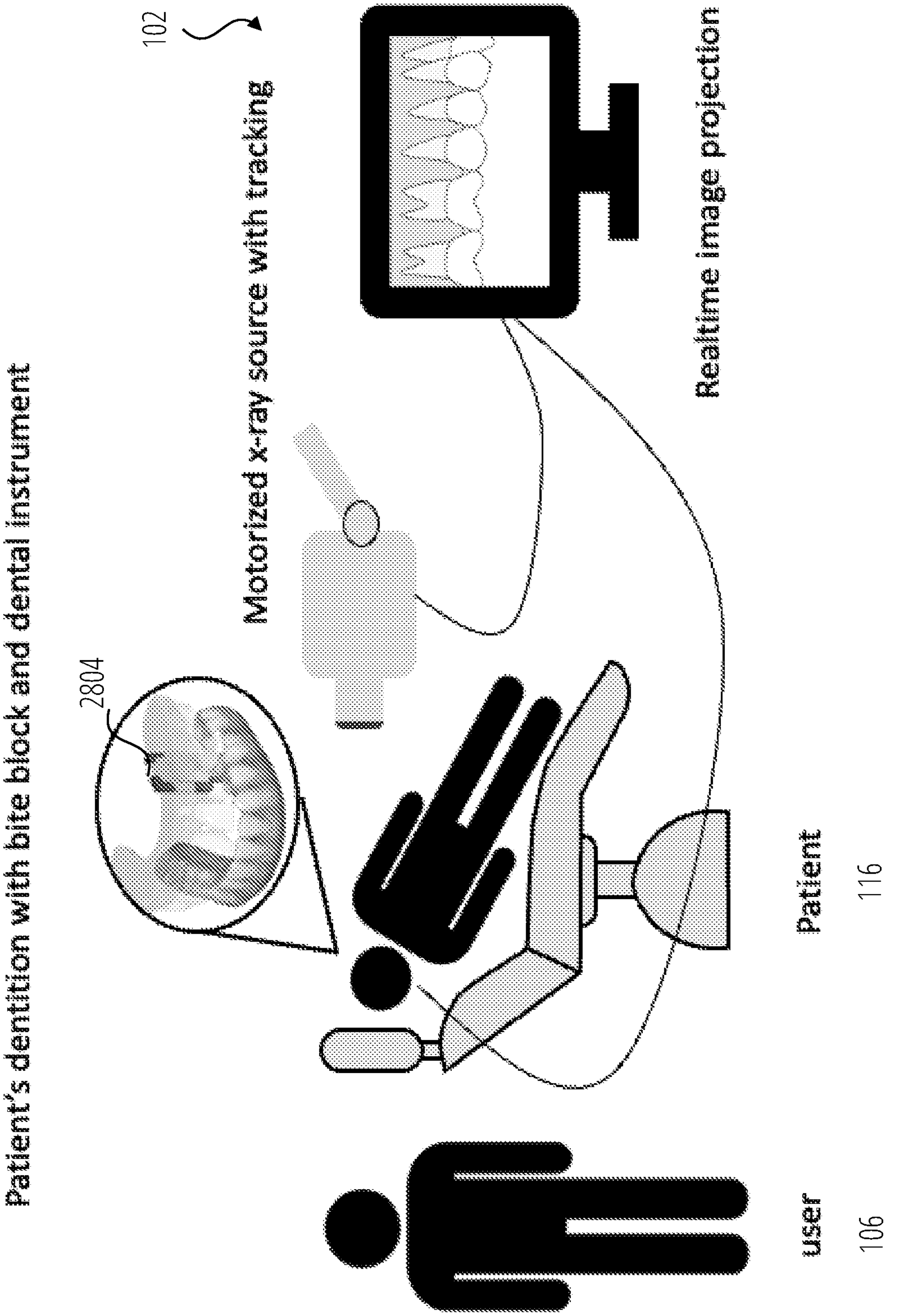
FIG. 34 illustrates an example configuration of an operation of the x-ray system in accordance with one example embodiment.

FIG. 34 illustrates an example configuration of an operation of the x-ray system in accordance with one example embodiment. The configuration includes the guidance system 102 directed at the x-ray sensor 2804 positioned between teeth of the patient 116. The technician 106 operates the guidance system 102.

Figure 35:
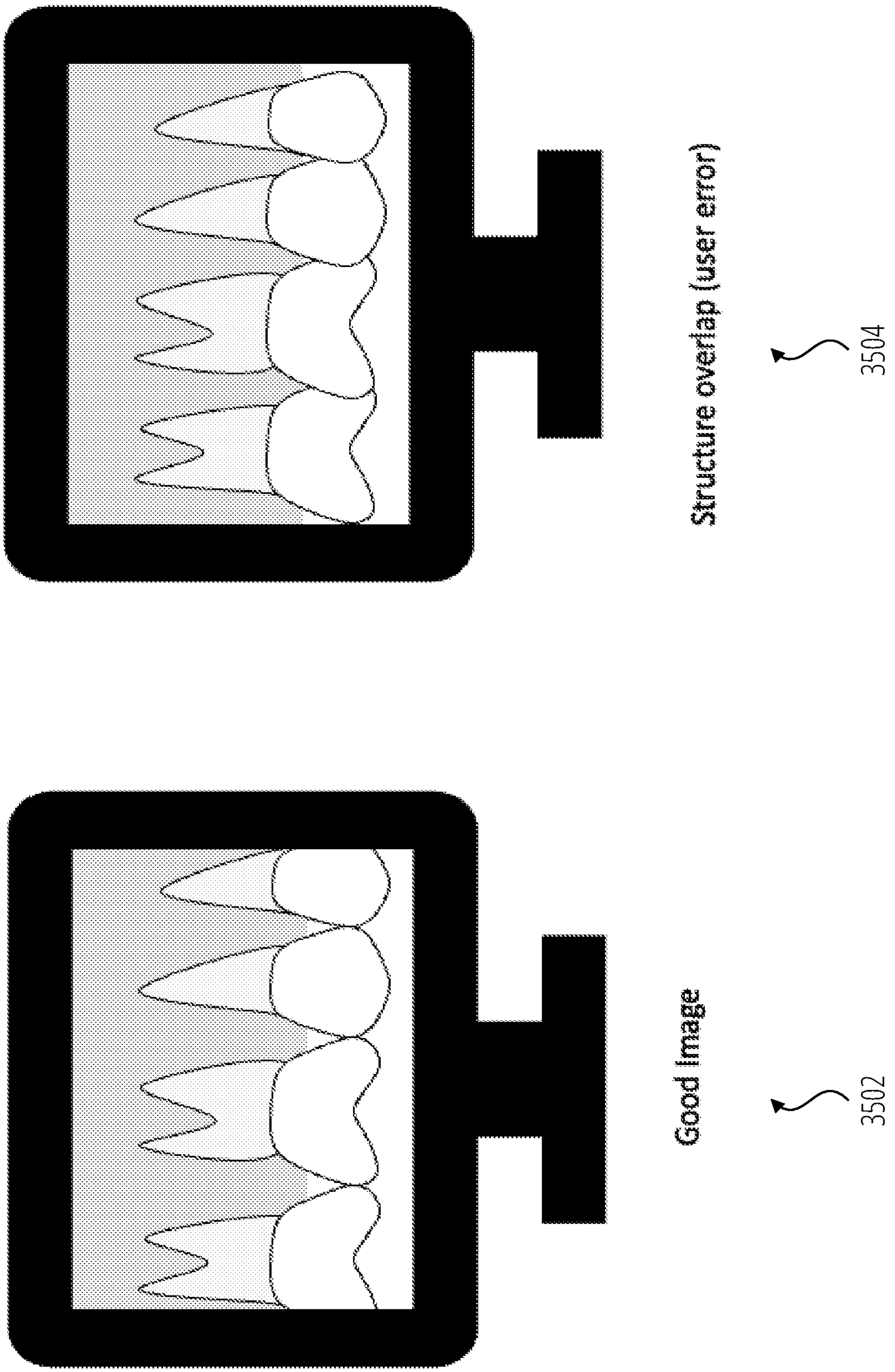
FIG. 35 illustrates an example of x-ray visualization in accordance with one example embodiment.

FIG. 35 illustrates an example of x-ray visualization in accordance with one example embodiment. The good image 3502 illustrates teeth structures that are not overlapped. The bad image 3504 illustrates structure overlap resulting from the technician 106 error (incorrect placement or aim).

Figure 36:
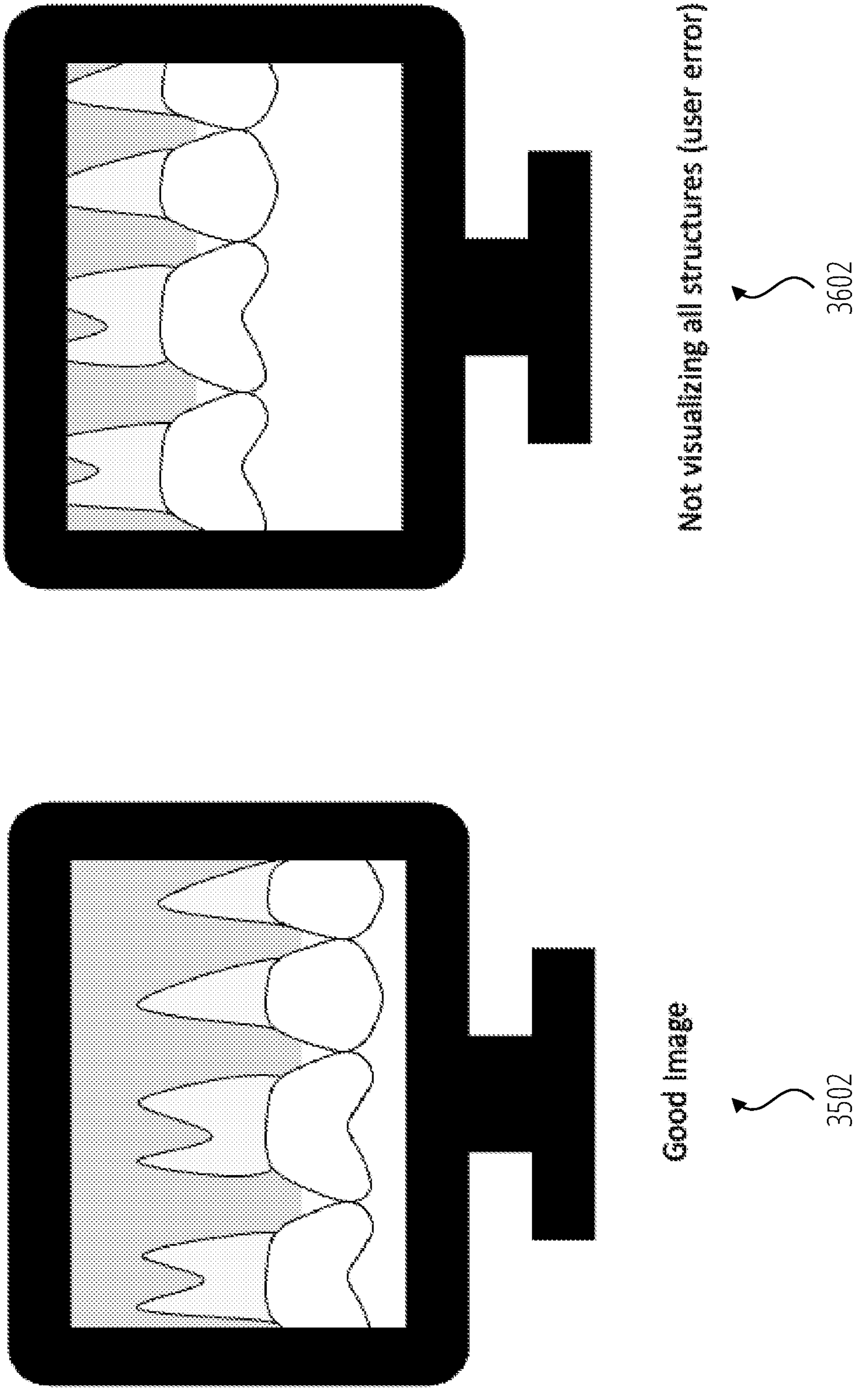
FIG. 36 illustrates an example of x-ray visualization in accordance with one example embodiment.

FIG. 36 illustrates an example of x-ray visualization in accordance with one example embodiment. The bad image 3602 illustrates structures that are not visible in their entirety.

Figure 37:
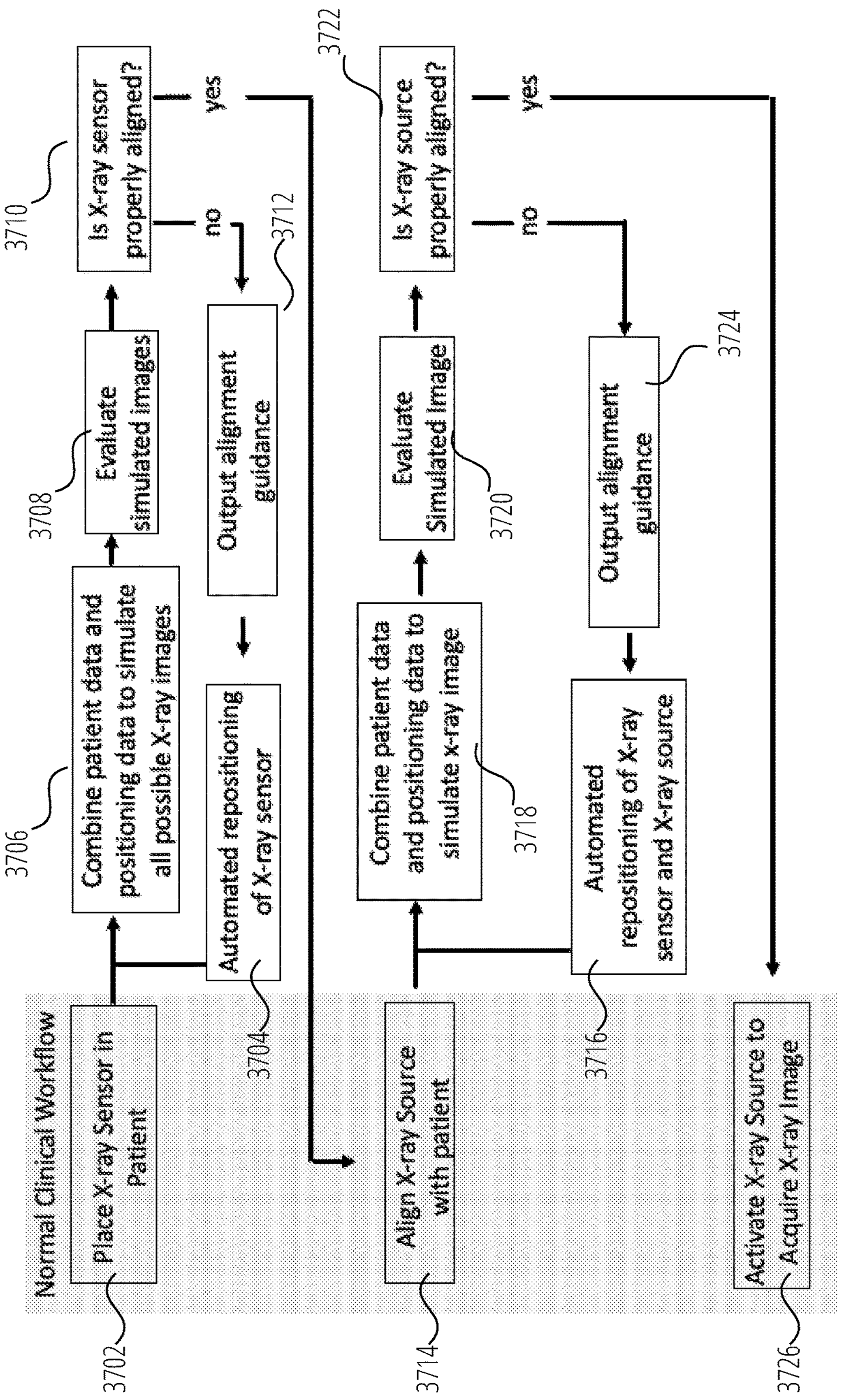
FIG. 37 is a flow diagram illustrating an example guidance operation of the x-ray system in accordance with one example embodiment.

FIG. 37 is a flow diagram illustrating an example guidance operation of the x-ray system in accordance with one example embodiment. A conventional clinical workflow includes block 3702, block 3714, and block 3726. At block 3702, the technician 106 places the x-ray sensor 120 in the patient 116's mouth. At block 3706, the imaging system 118 combines patient data and positioning data to simulate all possible x-ray images. At block 3708, the imaging system 118 evaluates the simulated images. At block 3710, the guidance system 102 determines whether the x-ray sensor 120 is properly aligned. If the guidance system 102 determines that the x-ray sensor 120 is not properly aligned, the guidance system 102 generates an output alignment guidance (e.g., a visual/audio feedback to prompt the technician 106 to move the x-ray sensor 120 in a specific direction by a specific amount). In another example, the guidance system 102 automatically repositions the x-ray sensor 120.

At block 3714, the technician 106 aligns the x-ray source 108 to the patient 116. At block 3718, the imaging system 118 combines patient data and positioning data to simulate the x-ray image. At block 3720, the technician 106 evaluates the simulated image. At block 3722, the guidance system 102 determines whether the x-ray source 108 is properly aligned. If the x-ray source 108 is properly aligned, the guidance system 102 generates an output alignment guidance. In one example, the guidance system 102 automatically repositions the location of the x-ray source 108 and/or the x-ray sensor 120. At block 3726, the technician 106 activates the x-ray source 108.

Figure 38:
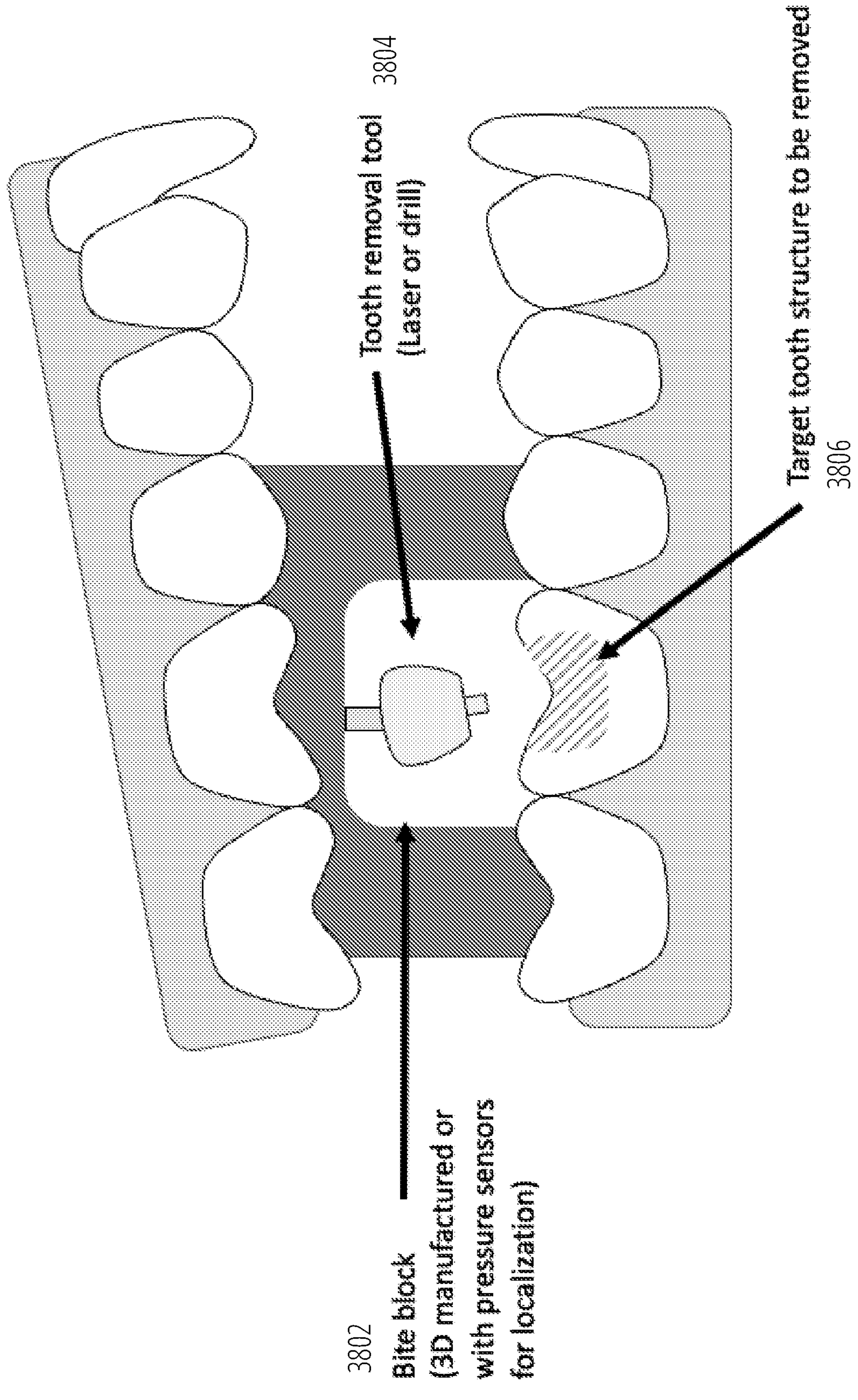
FIG. 38 is a block diagram illustrating a bite block in accordance with another example embodiment.

FIG. 38 is a block diagram illustrating a bite block in accordance with another example embodiment. The bite block 3802 illustrates a 3D manufactured bite block with pressure sensors placed at predefined locations in the bite block. The tooth removal drill 3804 is aimed at the target tooth 3806 based on the location data from the bite block 3802.

Figure 39:
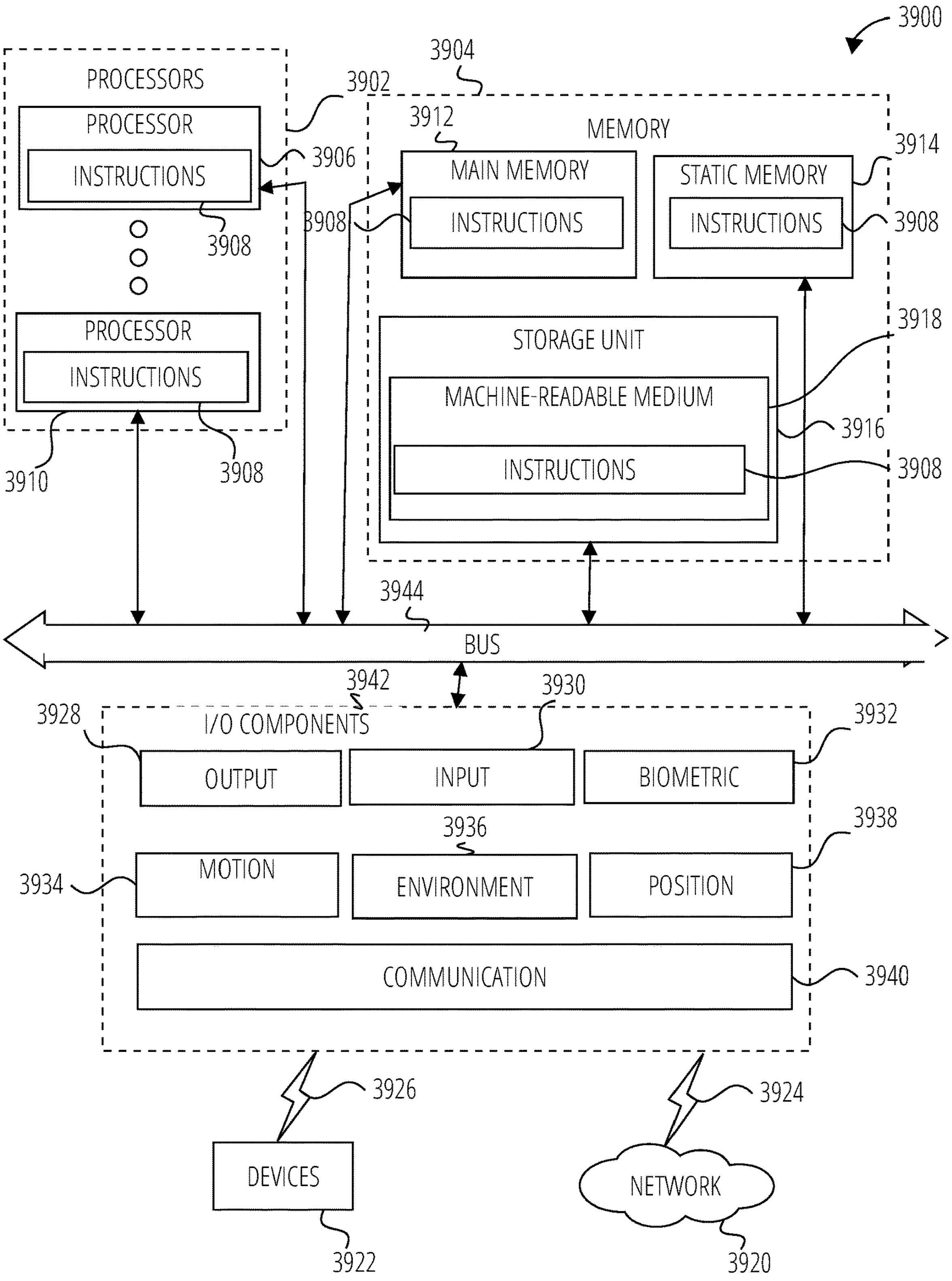
FIG. 39 is a diagrammatic representation of a machine in the form of a computer system within which a set of instructions may be executed for causing the machine to perform any one or more of the methodologies discussed herein, according to an example embodiment.

FIG. 39 is a diagrammatic representation of the machine 3900 within which instructions 3908 (e.g., software, a program, an application, an applet, an app, or other executable code) for causing the machine 3900 to perform any one or more of the methodologies discussed herein may be executed. For example, the instructions 3908 may cause the machine 3900 to execute any one or more of the methods described herein. The instructions 3908 transform the general, non-programmed machine 3900 into a particular machine 3900 programmed to carry out the described and illustrated functions in the manner described. The machine 3900 may operate as a standalone device or may be coupled (e.g., networked) to other machines. In a networked deployment, the machine 3900 may operate in the capacity of a server machine or a client machine in a server-client network environment, or as a peer machine in a peer-to-peer (or distributed) network environment. The machine 3900 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 3908, sequentially or otherwise, that specify actions to be taken by the machine 3900. Further, while only a single machine 3900 is illustrated, the term "machine" shall also be taken to include a collection of machines that individually or jointly execute the instructions 3908 to perform any one or more of the methodologies discussed herein.

The machine 3900 may include processors 3902, memory 3904, and I/O components 3942, which may be configured to communicate with each other via a bus 3944. In an example embodiment, the processors 3902 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an ASIC, a Radio-Frequency Integrated Circuit (RFIC), another Processor, or any suitable combination thereof) may include, for example, a Processor 3906 and a Processor 3910 that execute the instructions 3908. The term "Processor" is intended to include multi-core processors that may comprise two or more independent processors (sometimes referred to as "cores") that may execute instructions contemporaneously. Although FIG. 39 shows multiple processors 3902, the machine 3900 may include a single Processor with a single core, a single Processor with multiple cores (e.g., a multi-core Processor), multiple processors with a single core, multiple processors with multiples cores, or any combination thereof.

The memory 3904 includes a main memory 3912, a static memory 3914, and a storage unit 3916, both accessible to the processors 3902 via the bus 3944. The main memory 3904, the static memory 3914, and storage unit 3916 store the instructions 3908 embodying any one or more of the methodologies or functions described herein. The instructions 3908 may also reside, completely or partially, within the main memory 3912, within the static memory 3914, within machine-readable medium 3918 within the storage unit 3916, within at least one of the processors 3902 (e.g., within the Processor's cache memory), or any suitable combination thereof, during execution thereof by the machine 3900.

The I/O components 3942 may include a wide variety of components to receive input, provide output, produce output, transmit information, exchange information, capture measurements, and so on. The specific I/O components 3942 that are included in a particular machine will depend on the type of machine. For example, portable machines such as mobile phones may include a touch input device or other such input mechanisms, while a headless server machine will likely not include such a touch input device. It will be appreciated that the I/O components 3942 may include many other components that are not shown in FIG. 39. In various example embodiments, the I/O components 3942 may include output components 3928 and input components 3930. The output components 3928 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 3930 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 3942 may include biometric components 3932, motion components 3934, environmental components 3936, or position components 3938, among a wide array of other components. For example, the biometric components 3932 include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 3934 include acceleration sensor components (e.g., accelerometer), gravitation sensor components, rotation sensor components (e.g., gyroscope), and so forth. The environmental components 3936 include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 3938 include location sensor components (e.g., a GPS receiver Component), altitude sensor components (e.g., altimeters or barometers that detect air pressure from which altitude may be derived), orientation sensor components (e.g., magnetometers), and the like.

Communication may be implemented using a wide variety of technologies. The I/O components 3942 further include communication components 3940 operable to couple the machine 3900 to a network 3920 or devices 3922 via a coupling 3924 and a coupling 3926, respectively. For example, the communication components 3940 may include a network interface Component or another suitable device to interface with the network 3920. In further examples, the communication components 3940 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 3922 may be another machine or any of a wide variety of peripheral devices (e.g., a peripheral device coupled via a USB).

Moreover, the communication components 3940 may detect identifiers or include components operable to detect identifiers. For example, the communication components 3940 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 3940, such as location via Internet Protocol (IP) geolocation, location via Wi-Fi® signal triangulation, location via detecting an NFC beacon signal that may indicate a particular location, and so forth.

The various memories (e.g., memory 3904, main memory 3912, static memory 3914, and/or memory of the processors 3902) and/or storage unit 3916 may store one or more sets of instructions and data structures (e.g., software) embodying or used by any one or more of the methodologies or functions described herein. These instructions (e.g., the instructions 3908), when executed by processors 3902, cause various operations to implement the disclosed embodiments.

The instructions 3908 may be transmitted or received over the network 3920, using a transmission medium, via a network interface device (e.g., a network interface Component included in the communication components 3940) and using any one of a number of well-known transfer protocols (e.g., hypertext transfer protocol (HTTP)). Similarly, the instructions 3908 may be transmitted or received using a transmission medium via the coupling 3926 (e.g., a peer-to-peer coupling) to the devices 3922.

Although an embodiment has been described with reference to specific example embodiments, it will be evident that various modifications and changes may be made to these embodiments without departing from the broader scope of the present disclosure. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

EXAMPLES

Example 1 is a method comprising: accessing pressure sensor data from a pressure sensor being bitten by a patient; accessing occlusal pattern data corresponding to the patient; correlating the pressure sensor data with the occlusal pattern data; and identifying a location of the pressure sensor relative to teeth of the patient based on the correlated pressure sensor data with the occlusal pattern data.

Example 2 includes the method of example 1, further comprising: forming a frame of reference based on the location of the pressure sensor; identifying a location of an instrument relative to the frame of reference; and generating a display of a virtual representation of the instrument relative to a virtual representation of the teeth of the patient based on the location of the instrument relative to the frame of reference.

Example 3 includes the method of example 1, further comprising: accessing first imaging data of the teeth using a first sensor device, the first imaging data comprising volumetric data; accessing second imaging data of the teeth using a second sensor device, the second imaging data comprising surface data; and generating a composite image based on the first and second imaging data, the composite image indicating the volumetric data and the surface data of a specimen, wherein the first sensor device comprises a cone beam CT scanner, the first imaging data indicating bone volume of the specimen, wherein the second sensor device comprises an intraoral scanner.

Example 4 includes the method of example 3, further comprising: accessing third imaging data of a prepped tooth, the third imaging data comprising a digital surface scan of the prepped tooth; identifying features from teeth adjacent to the prepped tooth; registering the third imaging data with the composite image based on the features of the teeth adjacent to the prepped tooth; identifying an intersection of external treatment tooth geometry and the registered third imaging data; and determining a crown margin based on the identified intersection.

Example 5 includes the method of example 3, further comprising: determining clinical measurements of the teeth based on the first and second imaging data; and generating a three-dimensional (3D) model of the teeth based on the clinical measurements and the composite image.

Example 6 includes the method of example 5, further comprising: accessing a 2D image that indicates registration points; aligning the 2D image with the 3D model based on the registration points; and updating the 3D model based on the aligned 2D image.

Example 7 includes the method of example 6, further comprising: identifying anatomical discrepancies between the 2D image and the 3D model; and updating the 3D model based on the anatomical discrepancies.

Example 8 includes the method of example 1, further comprising: identifying a pose of an x-ray sensor relative to the teeth of the patient based on the location of the pressure sensor, the pressure sensor disposed at a preset location on the x-ray sensor; identifying a pose of an x-ray source relative to the pose of the x-ray sensor; and generating a simulated x-ray image based on the pose of the x-ray source relative to the pose of the x-ray sensor.

Example 9 includes the method of example 8, further comprising: generating a guidance based on the simulated x-ray image, the guidance indicating a suggested change to the pose of the x-ray sensor or the x-ray source.

Example 10 includes the method of example 8, further comprising: adjusting the pose of the x-ray source based on the simulated x-ray image.

Example 11 includes the method of example 8, wherein the x-ray sensor comprises the pressure sensor and a position sensor, the position sensor disposed at a predefined location on the x-ray sensor, wherein the pose of the x-ray sensor is based on the position sensor.

Example 12 includes the method of example 8, wherein the x-ray sensor comprises the pressure sensor and a visual marker, the visual marker disposed at a predefined location on the x-ray sensor.

Example 13 includes the method of example 12, wherein the x-ray source comprises a position sensor and an optical sensor, the optical sensor configured to capture an image of the visual marker, the position sensor being disposed at a predefined location on the x-ray source, wherein the pose of the x-ray source is based on the position sensor.

Example 14 includes the method of example 1, further comprising: providing a bite block comprising the pressure sensor and a tooth removal tool, the bite block configured to be temporarily locked with an upper and a lower jaw of the patient, the bite block forming a predefined frame of reference based on a position of the bite block relative to the teeth of the patient.

Example 15 includes the method of example 1, further comprising: accessing first sensor data of a reference object resting in a mouth of a patient, the reference object comprising the pressure sensor; accessing second sensor data of a sensor coupled to a dental instrument; determining a position of the dental instrument relative to the reference object based on the first and second sensor data; and displaying a virtual representation of the dental instrument relative to a virtual representation of the mouth of the patient based on the position of the dental instrument relative to the reference object.

Example 16 is a system comprising: an imaging system configured to: access pressure sensor data from a pressure sensor disposed between teeth of a patient, access occlusal pattern data of the patient, correlate the pressure sensor data with the occlusal pattern data, and identify a location of the pressure sensor relative to the teeth of the patient based on the correlated pressure sensor data with the occlusal pattern data; and a guidance system configured to: identify a pose of an x-ray sensor relative to the teeth of the patient based on the location of the pressure sensor, the pressure sensor disposed at a preset location on the x-ray sensor, identify a pose of an x-ray source relative to the pose of the x-ray sensor, generate a simulated x-ray image based on the pose of the x-ray source relative to the pose of the x-ray sensor.

Example 17 includes the system of example 16, wherein the imaging system is further configured to: form a frame of reference based on the location of the pressure sensor; identify a location of an instrument relative to the frame of reference; and generate a display of a virtual representation of the instrument relative to a virtual representation of the teeth of the patient based on the location of the instrument relative to the frame of reference.

Example 18 includes the system of example 16, wherein the imaging system is further configured to: access first imaging data of the teeth using a first sensor device, the first imaging data comprising volumetric data; access second imaging data of the teeth using a second sensor device, the second imaging data comprising surface data; and generate a composite image based on the first and second imaging data, the composite image indicating the volumetric data and the surface data of a specimen, wherein the first sensor device comprises a cone beam CT scanner, the first imaging data indicating bone volume of the specimen, wherein the second sensor device comprises an intraoral scanner.

Example 19 includes the system of example 16, wherein the guidance system comprises: a bite block comprising the pressure sensor and a tooth removal tool, the bite block configured to be temporarily locked with an upper and lower jaw of the patient, the bite block forming a predefined frame of reference based on a position of the bite block relative to the teeth of the patient.

Example 20 includes the system of example 16, wherein the guidance system is further configured to: generate a guidance based on the simulated x-ray image, the guidance indicating a suggested change to the pose of the x-ray sensor or the x-ray source.

What is claimed is:

1. A method comprising:

accessing pressure sensor data from a pressure sensor being bitten by a patient;

accessing occlusal pattern data corresponding to the patient;

correlating the pressure sensor data with the occlusal pattern data;

identifying a location of the pressure sensor relative to teeth of the patient based on the correlated pressure sensor data with the occlusal pattern data;

identifying a pose of an x-ray sensor relative to the teeth of the patient based on the location of the pressure sensor, the pressure sensor disposed at a preset location on the x-ray sensor;

identifying a pose of an x-ray source relative to the pose of the x-ray sensor; and generating a simulated x-ray image based on the pose of the x-ray source relative to the pose of the x-ray sensor.

2. The method of claim 1, further comprising:

forming a frame of reference based on the location of the pressure sensor;

identifying a location of an instrument relative to the frame of reference; and generating a display of a virtual representation of the instrument relative to a virtual representation of the teeth of the patient based on the location of the instrument relative to the frame of reference.

3. The method of claim 1, further comprising:

accessing first imaging data of the teeth using a first sensor device, the first imaging data comprising volumetric data;

accessing second imaging data of the teeth using a second sensor device, the second imaging data comprising surface data; and generating a composite image based on the first and second imaging data, the composite image indicating the volumetric data and the surface data of a specimen, wherein the first sensor device comprises a cone beam CT scanner, the first imaging data indicating bone volume of the specimen, wherein the second sensor device comprises an intraoral scanner.

4. The method of claim 3, further comprising:

accessing third imaging data of a prepped tooth, the third imaging data comprising a digital surface scan of the prepped tooth;

identifying features from teeth adjacent to the prepped tooth;

registering the third imaging data with the composite image based on the features of the teeth adjacent to the prepped tooth;

identifying an intersection of external treatment tooth geometry and the registered third imaging data; and determining a crown margin based on the identified intersection.

5. The method of claim 3, further comprising:

determining clinical measurements of the teeth based on the first and second imaging data; and generating a three-dimensional (3D) model of the teeth based on the clinical measurements and the composite image.

6. The method of claim 5, further comprising:

accessing a 2D image that indicates registration points;

aligning the 2D image with the 3D model based on the registration points; and updating the 3D model based on the aligned 2D image.

7. The method of claim 6, further comprising:

identifying anatomical discrepancies between the 2D image and the 3D model; and updating the 3D model based on the anatomical discrepancies.

8. The method of claim 1, further comprising:

generating a guidance based on the simulated x-ray image, the guidance indicating a suggested change to the pose of the x-ray sensor or the x-ray source.

9. The method of claim 1, further comprising:

adjusting the pose of the x-ray source based on the simulated x-ray image.

10. The method of claim 1, wherein the x-ray sensor comprises the pressure sensor and a position sensor, the position sensor disposed at a predefined location on the x-ray sensor, wherein the pose of the x-ray sensor is based on the position sensor.

11. The method of claim 1, wherein the x-ray sensor comprises the pressure sensor and a visual marker, the visual marker disposed at a predefined location on the x-ray sensor.

12. The method of claim 11, wherein the x-ray source comprises a position sensor and an optical sensor, the optical sensor configured to capture an image of the visual marker, the position sensor being disposed at a predefined location on the x-ray source, wherein the pose of the x-ray source is based on the position sensor.

13. The method of claim 1, further comprising:

providing a bite block comprising the pressure sensor and a tooth removal tool, the bite block configured to be temporarily locked with an upper and a lower jaw of the patient, the bite block forming a predefined frame of reference based on a position of the bite block relative to the teeth of the patient.

14. The method of claim 1, further comprising:

accessing first sensor data of a reference object resting in a mouth of a patient, the reference object comprising the pressure sensor;

accessing second sensor data of a sensor coupled to a dental instrument;

determining a position of the dental instrument relative to the reference object based on the first and second sensor data; and displaying a virtual representation of the dental instrument relative to a virtual representation of the mouth of the patient based on the position of the dental instrument relative to the reference object.

15. A system comprising:

an imaging system configured to: access pressure sensor data from a pressure sensor disposed between teeth of a patient, access occlusal pattern data of the patient, correlate the pressure sensor data with the occlusal pattern data, and identify a location of the pressure sensor relative to the teeth of the patient based on the correlated pressure sensor data with the occlusal pattern data; and a guidance system configured to: identify a pose of an x-ray sensor relative to the teeth of the patient based on the location of the pressure sensor, the pressure sensor disposed at a preset location on the x-ray sensor, identify a pose of an x-ray source relative to the pose of the x-ray sensor, generate a simulated x-ray image based on the pose of the x-ray source relative to the pose of the x-ray sensor.

16. The system of claim 15, wherein the imaging system is further configured to:

form a frame of reference based on the location of the pressure sensor;

identify a location of an instrument relative to the frame of reference; and generate a display of a virtual representation of the instrument relative to a virtual representation of the teeth of the patient based on the location of the instrument relative to the frame of reference.

17. The system of claim 15, wherein the imaging system is further configured to:

access first imaging data of the teeth using a first sensor device, the first imaging data comprising volumetric data;

access second imaging data of the teeth using a second sensor device, the second imaging data comprising surface data; and generate a composite image based on the first and second imaging data, the composite image indicating the volumetric data and the surface data of a specimen, wherein the first sensor device comprises a cone beam CT scanner, the first imaging data indicating bone volume of the specimen, wherein the second sensor device comprises an intraoral scanner.

18. The system of claim 15, wherein the guidance system comprises:

a bite block comprising the pressure sensor and a tooth removal tool, the bite block configured to be temporarily locked with an upper and lower jaw of the patient, the bite block forming a predefined frame of reference based on a position of the bite block relative to the teeth of the patient.

19. The system of claim 15, wherein the guidance system is further configured to:

generate a guidance based on the simulated x-ray image, the guidance indicating a suggested change to the pose of the x-ray sensor or the x-ray source.

* * * * *